United States Patent
Lin et al.

(10) Patent No.: US 11,981,617 B2
(45) Date of Patent: May 14, 2024

(54) KETAMINE PAMOATE AND USE THEREOF

(71) Applicant: Alar Pharmaceuticals Inc., Taichung (TW)

(72) Inventors: Tong-Ho Lin, Taichung (TW); Yung-Shun Wen, Taichung (TW); Chia-Hsien Chen, Taichung (TW); Wei-Ju Chang, Taichung (TW)

(73) Assignee: Alar Pharmaceuticals Inc., Taichung (TW)

( * ) Notice: Subject to any disclaimer, the term of this patent is extended or adjusted under 35 U.S.C. 154(b) by 416 days.

(21) Appl. No.: 17/421,407

(22) PCT Filed: Jan. 10, 2020

(86) PCT No.: PCT/CN2020/071404
§ 371 (c)(1),
(2) Date: Jul. 8, 2021

(87) PCT Pub. No.: WO2020/143762
PCT Pub. Date: Jul. 16, 2020

(65) Prior Publication Data
US 2022/0119338 A1  Apr. 21, 2022

Related U.S. Application Data

(60) Provisional application No. 62/871,763, filed on Jul. 9, 2019, provisional application No. 62/791,058, filed on Jan. 11, 2019.

(51) Int. Cl.
*C07C 211/35* (2006.01)
*A61P 25/24* (2006.01)

(52) U.S. Cl.
CPC ............ *C07C 211/35* (2013.01); *A61P 25/24* (2018.01); *C07B 2200/13* (2013.01); *C07C 2601/14* (2017.05); *C07C 2601/16* (2017.05)

(58) Field of Classification Search
CPC .... C07C 211/35; C07B 2200/13; A61P 25/24; A61P 25/28
See application file for complete search history.

(56) References Cited

U.S. PATENT DOCUMENTS

| | | | |
|---|---|---|---|
| 9,421,266 B2* | 8/2016 | King | A61K 47/22 |
| 10,836,714 B2* | 11/2020 | Xiang | C07D 213/82 |
| 2008/0293695 A1 | 11/2008 | Bristol et al. | |
| 2014/0178480 A1 | 6/2014 | King et al. | |
| 2019/0350877 A1 | 11/2019 | Kandula | |

FOREIGN PATENT DOCUMENTS

CN    106562952    4/2017

OTHER PUBLICATIONS

International Search Report and Written Opinion for International Application No. PCT/CN2020/071404 dated Apr. 8, 2020, 6 pages.

* cited by examiner

*Primary Examiner* — Sikarl A Witherspoon
(74) *Attorney, Agent, or Firm* — Amin, Turocy & Watson, LLP

(57) ABSTRACT

Provided are pamoate salts of ketamine having a stoichiometry of 2:1 of ketamine to pamoate, including R, S-ketamine pamoate, S-ketamine pamoate, or R-ketamine pamoate, and crystalline or amorphous forms of the pamoate salts, and having excellent safety and properties for pharmaceutical applications. Also provided are pharmaceutical compositions including the pamoate salts of ketamine and their uses in treating a CNS disease or serving as an anesthetic.

13 Claims, 37 Drawing Sheets

KETAMINE PAMOATE AND USE THEREOF

TECHNICAL FIELD

The present disclosure relates to the field of medicinal chemistry. More specifically, the present disclosure relates to salts of ketamine in a crystal or amorphous form, and pharmaceutical uses thereof.

BACKGROUND

Ketamine is a racemic mixture containing equal amounts of S-ketamine and R-ketamine, which are also called as the S-isomer and R-isomer of ketamine and represented by the following formulas:

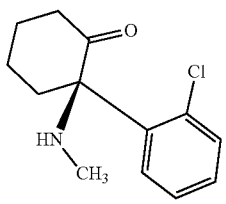
(R)-Ketamine

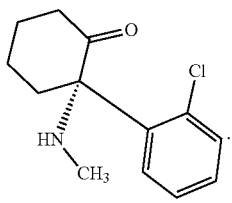
(S)-Ketamine

Ketamine is an N-methyl-D-aspartate (NMDA) receptor (NMDAR) antagonist. Its pharmacodynamic characteristic is reported as anesthesia, analgesia, or antidepressant, and is also relevant to treat some central nervous system (CNS) diseases such as the pathogenesis associated with NMDAR-mediated excitotoxicity and inflammatory neurodegenerative effects, which include Alzheimer's disease, Parkinson's disease, stroke and traumatic brain injury (TBI), and multiple sclerosis (MS) [1-3].

Ketamine has been used as anesthetic and antidepressant drug products. Moreover, it also has a specific characteristic of rapid onset, which can improve depressive symptoms within 24 hours following treatment. For instance, R, S-ketamine HCl has been marketed since 1970 as Ketalar injection (Pfizer) for anesthetic use. In addition, an intranasal product of S-ketamine HCl, Spravato nasal spray, has been approved by FDA in 2019 for treatment-resistant depression (TRD).

At present, ketamine (including S-isomer and R-isomer) is not only known to be used for anesthesia, analgesia, antidepressant and anti-inflammatory [4], but is one of the drugs that have attracted attention for major depressive disorders (MDD), MDD with imminent risk of suicidal ideation, TRD, bipolar disorder, obsessive-compulsive disorder, posttraumatic stress disorder (hereinafter abbreviated PTSD), autism spectrum disorder, tinnitus, refractory chronic migraine, asthma, anxiety, substance use disorders, alcohol use disorder, eating disorders, refractory status epilepticus, and brain ischemia by clinical or nonclinical researches [5-23].

However, ketamine has problems with side effects including psychotic symptoms such as hallucination, delusion, dependence, and abuse liability. The clinical adverse effects have been found, including psychotic effects such as dissociation, nervous system disorders such as dizziness and sedation, memory and cognitive impairment, direct or indirect peripheral effects such as tachycardia, mild respiratory depression, hypertension, palpitation, musculoskeletal effects (myoclonus, twitching, spasms, ataxia, fasciculation), and urological complications (dysuria, increased frequency and urgency of urination, incontinence, pain, hematuria, and ulcerative cystitis) [4, 24]. The major incidences of adverse effects are psychiatric and nervous system disorders, including dissociation and sedation [4]. In addition, ketamine-related animal toxicology effects include neurotoxicity, bladder and renal toxicity, and heart-related toxicities [25].

Therefore, it is an object of the present disclosure to provide a pharmaceutical composition, which is safe for patients and effectively provides a therapeutic effect without adversely affecting body functions of the patients.

SUMMARY

In view of the foregoing, the present disclosure provides pamoate salts of ketamine and polymorphs thereof. In one embodiment of the present disclosure, the pamoate salt of ketamine has a stoichiometry of 2:1 of ketamine to pamoate. In another embodiment, the ketamine may be S-ketamine, R-ketamine, or R, S-ketamine (a racemic mixture containing equal amounts of S-ketamine and R-ketamine).

In one embodiment of the present disclosure, the pamoate salt of ketamine is R, S-ketamine pamoate, S-ketamine pamoate, or R-ketamine pamoate, which are represented by the following Formulas (I), (II), and (III), respectively:

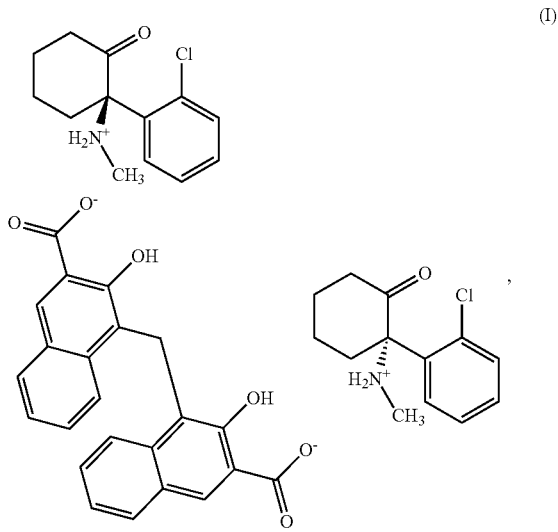
(I)

-continued

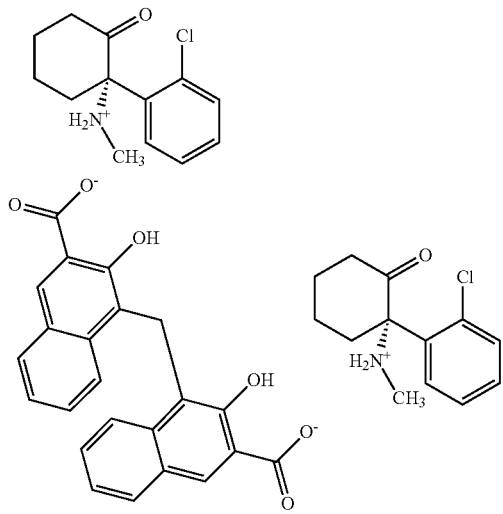

(II)

(III)

In one embodiment of the present disclosure, the pamoate salt of ketamine may be amorphous or crystalline. In another embodiment, the crystalline form of the pamoate salt of ketamine is represented by an x-ray powder diffraction (XRPD) pattern comprising one or more 2θ values selected from 6.0, 10.7, 11.6, 12.0, 13.0, 14.7, 15.0, 19.6, 22.2, 25.2 and 30.3 (±0.2 2θ).

In one embodiment of the present disclosure, the pamoate salt of ketamine is R, S-ketamine pamoate in crystalline form represented by an XRPD pattern comprising one or more 2θ values selected from 6.0, 8.6, 10.7, 11.6, 12.0, 13.0, 14.7, 15.0, 15.3, 17.9, 18.6, 19.6, 20.0, 21.1, 21.6, 22.2, 23.3, 24.4, 25.2, 25.9, 26.9, 28.6, 29.7, 30.3, 32.4, 34.0 and 36.6 (±0.2 2θ).

In one embodiment of the present disclosure, the pamoate salt of ketamine is S-ketamine pamoate in crystalline form represented by an XRPD pattern comprising one or more 2θ values selected from 6.0, 10.8, 11.7, 12.0, 12.6, 13.1, 14.6, 15.1, 18.2, 19.2, 19.7, 20.1, 22.0, 22.8, 23.3, 23.7, 24.1, 24.7, 25.2, 27.3, 30.1, 31.6, 45.4, 56.4 and 75.2 (±0.2 2θ).

In one embodiment of the present disclosure, the pamoate salt of ketamine is R-ketamine pamoate in crystalline form represented by an XRPD pattern comprising one or more 2θ values selected from 6.0, 10.8, 11.7, 12.0, 12.6, 13.1, 14.6, 15.0, 18.2, 19.3, 19.7, 20.6, 22.0, 22.9, 23.6, 24.1, 24.7, 25.2, 25.9, 27.3, 30.1, 31.6, 45.4, 56.4 and 75.2 (±0.2 2θ).

In one embodiment of the present disclosure, the pamoate salt of ketamine is in crystalline form represented by an XRPD pattern substantially in accordance with the pattern shown in FIG. 2A, FIG. 2B, or FIG. 2C.

In one embodiment of the present disclosure, the pamoate salt of ketamine has a purity of greater than 95%. In another embodiment, the pamoate salt of ketamine has a purity of greater than 99%, such as 99.5%, 99.6%, 99.7%, 99.8%, 99.9% and substantially 100%.

The present disclosure also provides a pharmaceutical composition that is applicable to be antidepressant, anti-inflammatory, anesthetic and analgesic administration. In one embodiment of the present disclosure, the pharmaceutical composition comprises the above pamoate salt of ketamine and a pharmaceutically acceptable excipient thereof.

In one embodiment of the present disclosure, the pharmaceutical composition is used for treating a CNS disease, wherein an effective amount of the pharmaceutical composition is to be administered to a subject in need thereof.

In one embodiment of the present disclosure, the pharmaceutical composition is used for anesthetizing a subject in need thereof, with an effective amount of the pharmaceutical composition being administered to the subject.

In one embodiment of the present disclosure, the treatment of the CNS disease lasts for at least 10 days after administration of the pharmaceutical composition. In another embodiment, the pharmaceutical composition may provide antidepressant, anti-inflammatory, anesthetic or analgesic effects lasting for at least about 10 days.

In the present disclosure, it is provided with a pamoate salt of ketamine and a polymorph thereof, which may be used as an antidepressant, an anti-inflammatory agent, an anesthetic or an analgesic with the improved safety than ketamine or ketamine HCl, and thus could overcome the application restrictions of ketamine. Hence, the salts of ketamine and the polymorphs thereof provided in the present disclosure have excellent properties for pharmaceutical applications.

BRIEF DESCRIPTION OF THE DRAWINGS

The present disclosure can be more fully understood by reading the following descriptions of the embodiments, with reference made to the accompanying drawings.

FIGS. 12A to 12F are hematoxylin and eosin (HE) staining images of rat injection site tissues, in which FIGS. 12A, 12C, and 12E are representative images of ketamine HCl injection site tissues under ×40, ×100, and ×400 magnification, respectively, and FIGS. 12B, 12D, and 12F are representative images of R, S-ketamine pamoate injection site tissues under ×40, ×100, and ×400 magnification, respectively. Black stars indicate inflammatory cells.

FIGS. 13A to 13F are HE staining images of rat bladder tissues, in which FIGS. 13A and 13D are representative images of Control rat bladder tissues under ×400 and ×40 magnification, respectively; FIGS. 13B and 13E are representative images of KET rat bladder tissues under ×400 and ×40 magnification, respectively; and FIGS. 13C and 13F are representative images of KEP rat bladder tissues under ×400 and ×40 magnification, respectively.

FIGS. 14A to 14F are HE staining images of rat brain tissues at prefrontal cortex, in which FIGS. 14A and 14D are representative images of Control rat brain tissues under ×100 and ×400 magnification, respectively; FIGS. 14B and 14E are representative images of KET rat brain tissues under ×100 and ×400 magnification, respectively; and FIGS. 14C and 14F are representative images of KEP rat brain tissues under ×100 and ×400 magnification, respectively. Black stars indicate granule cells. Black arrows indicate pyramidal cells.

DETAILED DESCRIPTION

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the above examples for carrying out this disclosure without contravening its scope, for different aspects and applications.

It is further noted that, as used in this disclosure, the singular forms "a," "an," and "the" include plural referents, unless expressly and unequivocally limited to one referent. The term "or" is used interchangeably with the term "and/or" unless the context clearly indicates otherwise.

The present disclosure is directed to a pamoate salt of ketamine with a ratio of ketamine to pamoate of 2:1.

In one embodiment, the pamoate salt of ketamine may be amorphous or in a crystalline form characterized by an XRPD pattern comprising one, two, three, four, five, six, seven, eight, nine, ten or more 2θ values selected from 6.0, 10.7, 11.6, 12.0, 13.0, 14.7, 15.0, 19.6, 22.2, 25.2 and 30.3 (±0.2 2θ). In another embodiment, the 2θ values are measured by using CuKα radiation at room temperature.

Figure 2A:
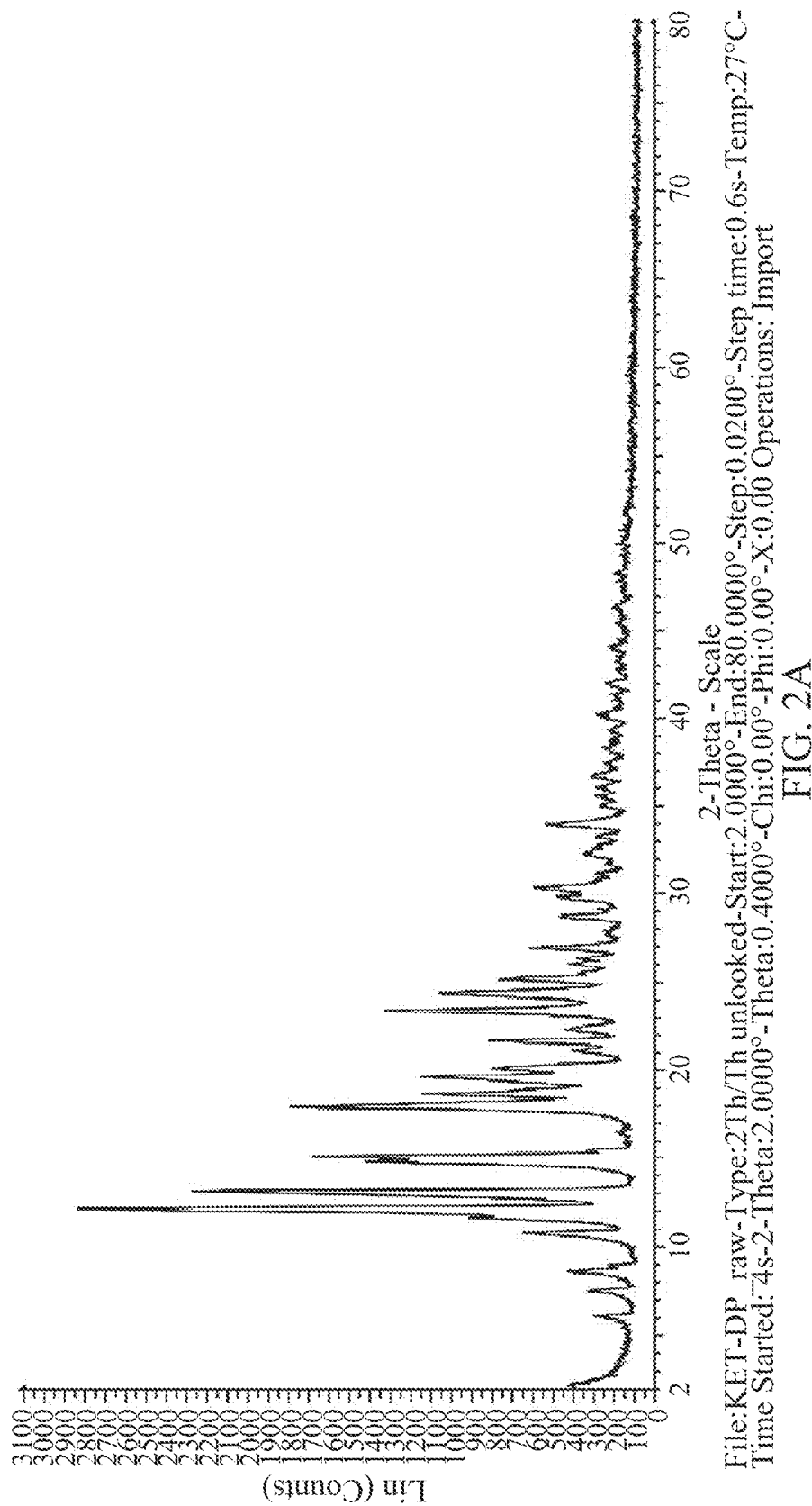
FIGS. 2A to 2F illustrate the X-ray powder diffraction patterns of R, S-ketamine pamoate, S-ketamine pamoate, and R-ketamine pamoate in crystal form (FIGS. 2A to 2C) or amorphous form (FIGS. 2D to 2F), respectively.

In one embodiment, the present disclosure provides a crystalline R, S-ketamine pamoate salt that has an XRPD pattern comprising one, two, three, four, five, six, seven, eight, nine, ten or more 2θ values selected from 6.0, 10.7, 11.6, 12.0, 13.0, 14.7, 15.0, 19.6, 22.2, 25.2 and 30.3 (±0.2 2θ), or one, two, three, four, five, six, seven, eight, nine, ten or more 2θ values selected from 8.6, 15.3, 17.9, 18.6, 20.0, 21.1, 21.6, 23.4, 24.4, 25.9, 26.9, 28.6, 29.7, 32.4, 34.0 and 36.6 (±0.2 2θ). In another embodiment, the crystalline R, S-ketamine pamoate salt has an XRPD pattern represented by at least one of the following: (i) the XRPD pattern comprising one, two, three, four, five, six, seven, eight, nine, ten or more 2θ values selected from 6.0, 8.6, 10.7, 11.6, 12.0, 13.0, 14.7, 15.0, 15.3, 17.9, 18.6, 19.6, 20.0, 21.1, 21.6, 22.2, 23.3, 24.4, 25.2, 25.9, 26.9, 28.6, 29.7, 30.3, 32.4, 34.0 and 36.6 (±0.2 2θ); and (ii) the XRPD pattern shown in FIG. 2A. In yet another embodiment, the crystalline R, S-ketamine pamoate salt has an XRPD pattern as shown in FIG. 2A.

Figure 2B:
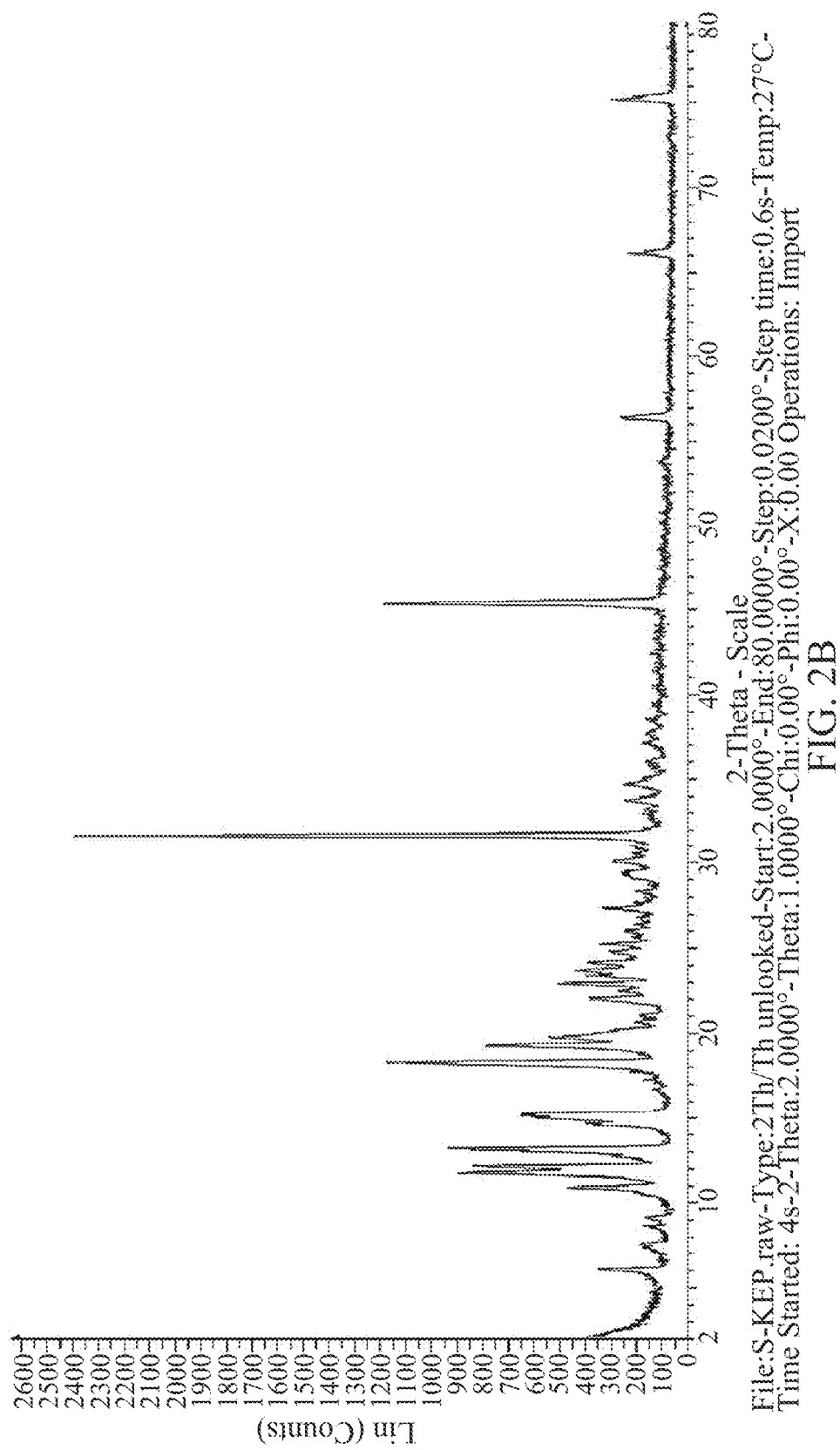

In one embodiment, the present disclosure provides a crystalline S-ketamine pamoate salt that has an XRPD pattern comprising one, two, three, four, five, six, seven, eight, nine, ten or more 2θ values selected from 6.0, 10.8, 11.7, 12.0, 13.1, 14.6, 15.1, 19.7, 22.0, 25.2 and 30.1 (±0.2 2θ), or one, two, three, four, five, six, seven, eight, nine, ten or more 2θ values selected from 12.6, 18.2, 19.2, 20.1, 22.8, 23.3, 23.7, 24.1, 24.7, 27.3, 31.6, 45.4, 56.4 and 75.2 (±0.2 2θ). In another embodiment, the crystalline S-ketamine pamoate salt has an XRPD pattern represented by at least one of the following: (i) the XRPD pattern comprising one, two, three, four, five, six, seven, eight, nine, ten or more 2θ values selected from 6.0, 10.8, 11.7, 12.0, 12.6, 13.1, 14.6, 15.1, 18.2, 19.2, 19.7, 20.1, 22.0, 22.8, 23.3, 23.7, 24.1, 24.7, 25.2, 27.3, 30.1, 31.6, 45.4, 56.4 and 75.2 (±0.2 2θ); and (ii) the XRPD pattern shown in FIG. 2B. In yet another embodiment, the crystalline S-ketamine pamoate salt has an XRPD pattern as shown in FIG. 2B.

Figure 2C:
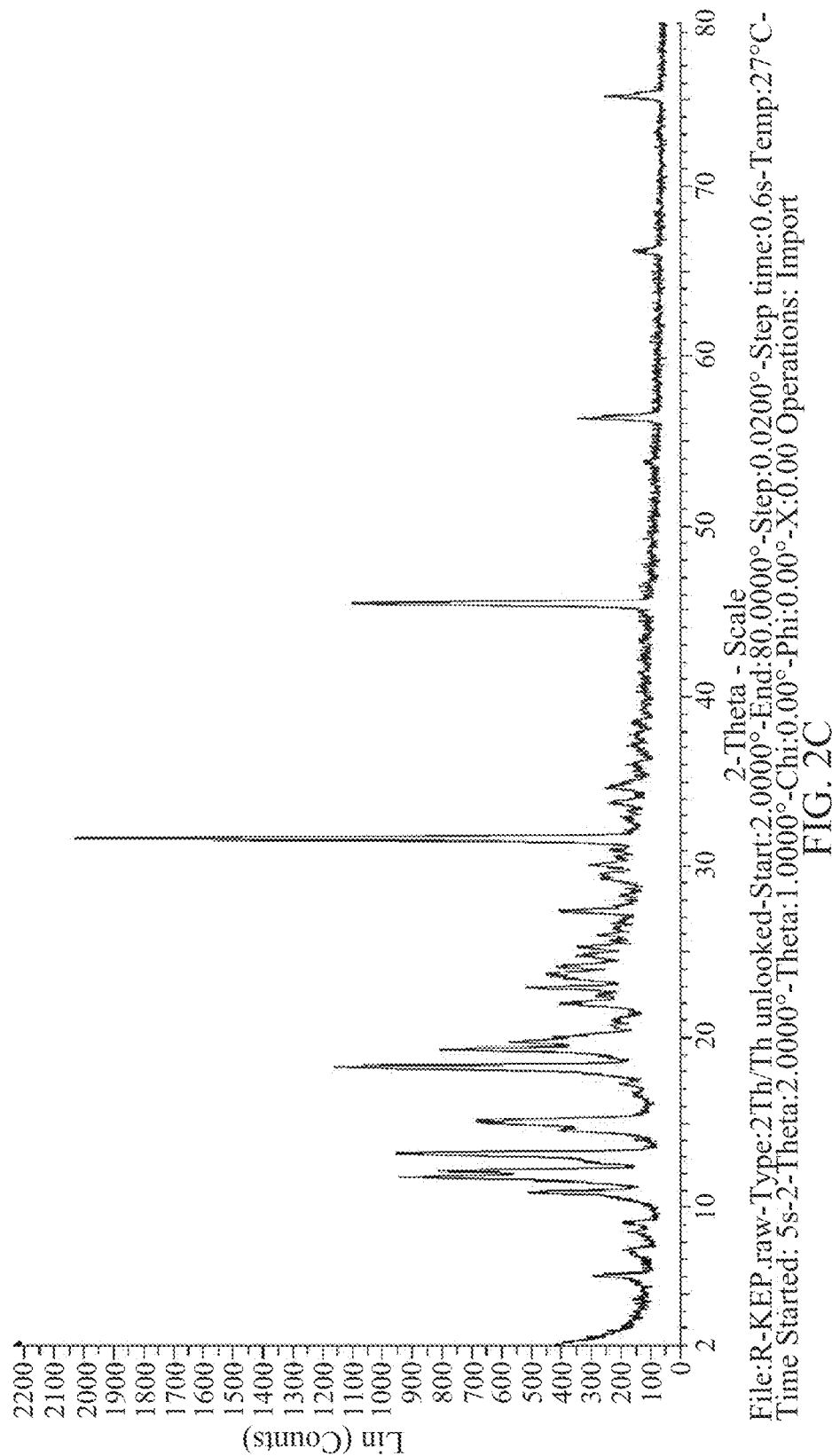
Figure 2D:
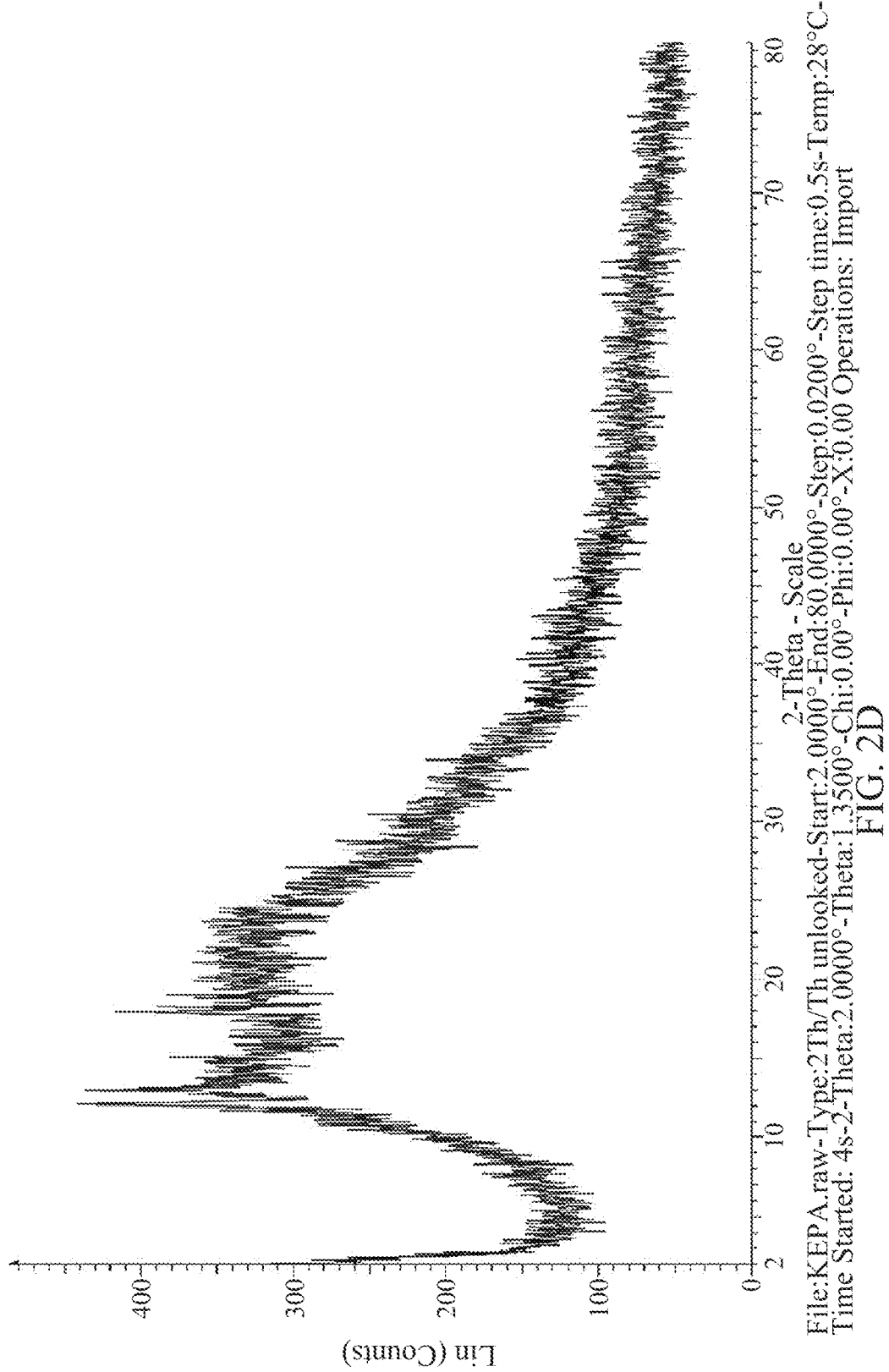
Figure 2E:
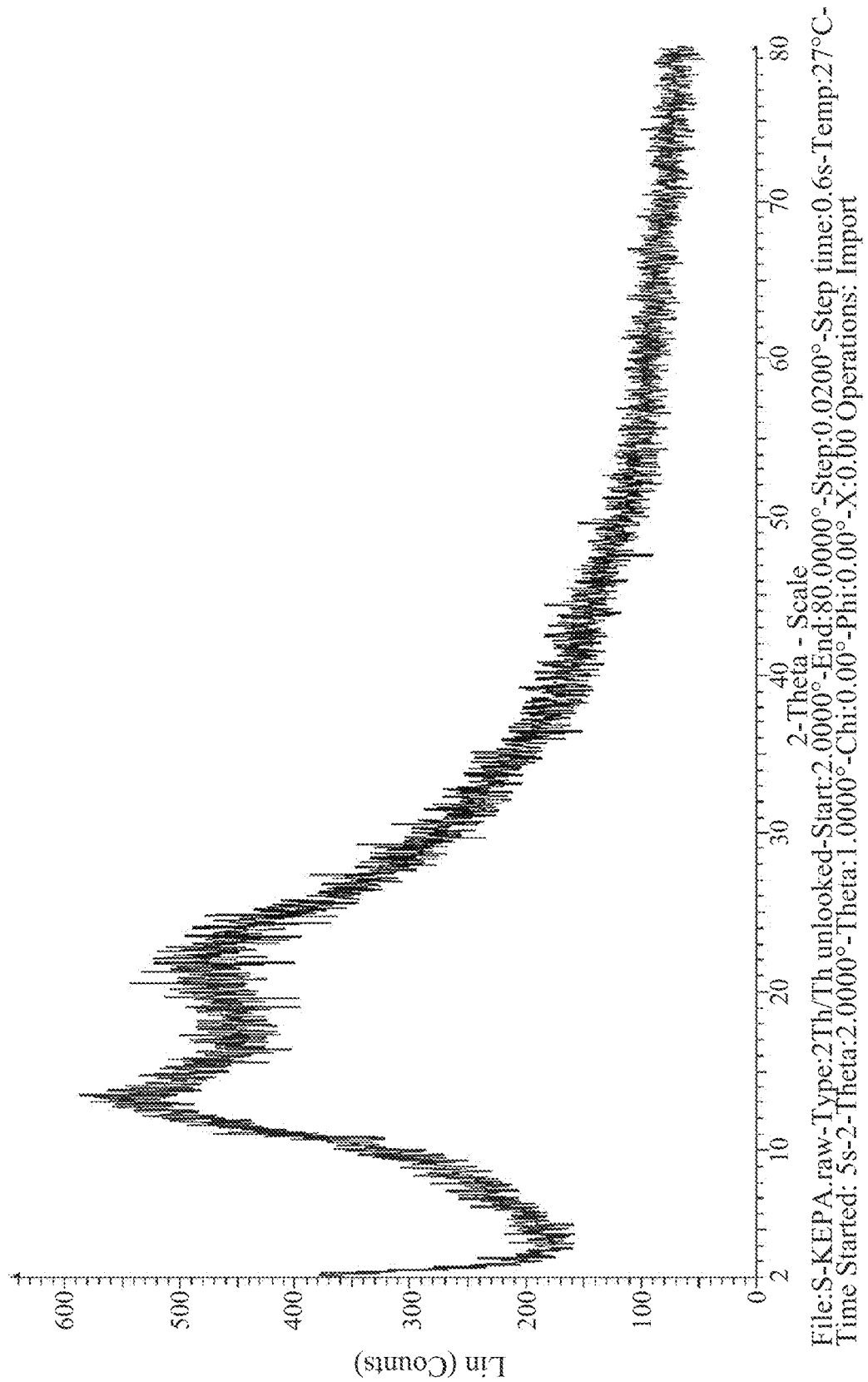
Figure 2F:
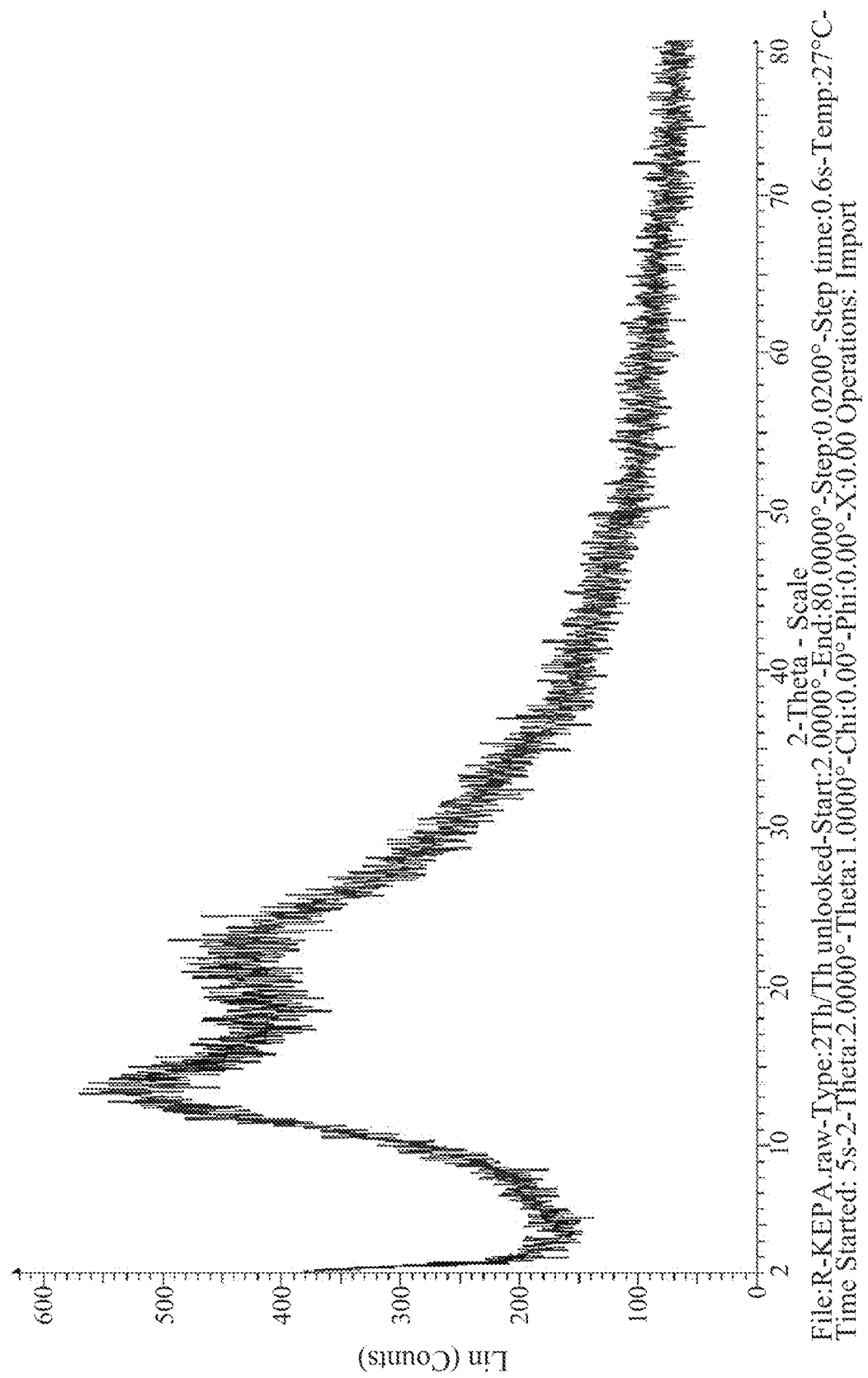

In one embodiment, the present disclosure provides a crystalline R-ketamine pamoate salt that has an XRPD pattern comprising one, two, three, four, five, six, seven, eight, nine, ten or more 2θ values selected from 6.0, 10.8, 11.7, 12.0, 13.1, 14.6, 15.0, 19.7, 22.0, 25.2 and 30.1 (±0.2 2θ), or one, two, three, four, five, six, seven, eight, nine, ten or more 2θ values selected from 12.6, 18.2, 19.3, 20.6, 22.9, 23.6, 24.1, 24.7, 25.9, 27.3, 31.6, 45.4, 56.4 and 75.2 (±0.2 2θ). In another embodiment, the crystalline R-ketamine pamoate salt has an XRPD pattern represented by at least one of the following: (i) the XRPD pattern comprising one, two, three, four, five, six, seven, eight, nine, ten or more 2θ values selected from 6.0, 10.8, 11.7, 12.0, 12.6, 13.1, 14.6, 15.0, 18.2, 19.3, 19.7, 20.6, 22.0, 22.9, 23.6, 24.1, 24.7, 25.2, 25.9, 27.3, 30.1, 31.6, 45.4, 56.4 and 75.2 (±0.2 2θ); and (ii) the XRPD pattern shown in FIG. 2C. In yet another embodiment, the crystalline R-ketamine pamoate salt has an XRPD pattern as shown in FIG. 2C.

The present disclosure is also directed to a method of treating a subject suffering from a CNS disease, comprising administering to the subject an effective amount of a pharmaceutical composition comprising a pamoate salt of ketamine and a pharmaceutically acceptable excipient thereof.

In one embodiment, the CNS disease may include, but is not limited to, MDD, MDD with imminent risk of suicidal ideation, TRD, bipolar disorder, obsessive-compulsive disorder, PTSD, autism spectrum disorder, tinnitus, refractory chronic migraine, asthma, anxiety, substance use disorders, alcohol use disorder, eating disorders, refractory status epilepticus, brain ischemia, Alzheimer's disease, Parkinson's disease, stroke, traumatic brain injury, multiple sclerosis, and pain.

The present disclosure is also directed to a method of anesthetizing a subject in need thereof, comprising administering to the subject an effective amount of a pharmaceutical composition comprising a pamoate salt of ketamine and a pharmaceutically acceptable excipient thereof.

The term "patient" or "subject" as used interchangeably herein in the context of a therapy refers to a human or a non-human animal, as the recipient of a therapy or preventive care.

As used herein, the term "treating" or "treatment" refers to administration of an effective amount of a pamoate salt of ketamine, a polymorph thereof, or a pharmaceutical composition containing the same to a subject in need thereof to cure, alleviate, relieve, remedy, ameliorate, or prevent a disease, the symptom thereof, or the predisposition towards it. Such a subject can be identified by a health care professional based on results from any suitable diagnostic method.

As used herein, the term "effective amount" refers to a therapeutic amount that is sufficient to result in prevention of the development, recurrence, or onset of a CNS disease and one or more symptoms thereof, enhance or improve a prophylactic effect of another therapy, reduce the severity or duration of a disorder, ameliorate one or more symptoms of a disorder, prevent the advancement of a psychotic disorder or an inflammatory disorder, and/or enhance or improve a therapeutic effect of another therapy.

As used herein, the phrase "pharmaceutically acceptable" refers a substance that is acceptable for use in pharmaceutical applications from a toxicological perspective and does not adversely interact with an active ingredient.

Depending on the type of pharmaceutical compositions, the pharmaceutically acceptable excipient may be chosen from any one or a combination of excipients known in the art. The choice of the pharmaceutically acceptable excipient depends partly upon the desired method of administration to be used. For a pharmaceutical composition of the present disclosure, an excipient should be chosen so as to substantially maintain the particular form of an active compound (e.g., a ketamine pamoate salt), whether it be crystalline or not. In other words, the excipient would not substantially alter the form the active compound is. Nor would the excipient be otherwise incompatible with the form of an active compound, such as by producing any undesirable biological effect or otherwise interacting in a deleterious manner with any other component(s) of the pharmaceutical composition.

In certain embodiments of the present disclosure, the pharmaceutical composition is administered to the subject orally, intravenously, intramuscularly, subcutaneously, intraperitoneally, intradermally, transdermally, intranasally, rectally, intrathecally, intramucosally, or intraoculariy.

In certain embodiments of the present disclosure, the pharmaceutical composition of the present disclosure is formulated in a form suitable for oral administration, and thus the pharmaceutical composition may be administered to the subject by oral delivery. Alternatively, the pharmaceutical composition may be formulated in a form of dry powder, a tablet, a lozenge, a capsule, granule, or a pill.

The pharmaceutical composition of the present disclosure may only comprise the ketamine pamoate salt as an active ingredient for anesthetic use and treating a CNS disease. In other words, the ketamine pamoate salt may serve as the only active ingredient as being an anesthetic and preventing or treating a CNS disease in the composition. In this embodiment, the present disclosure provides a safe and effective therapy for treating a CNS disease or anesthesia by the use of the ketamine pamoate salt alone as the active ingredient. Alternatively, in another embodiment, the pharmaceutical composition may include or be administered to a subject in combination with another active ingredient unless the effect of the disclosure is inhibited.

In one embodiment, a therapeutic effect provided by the ketamine pamoate salts of the present disclosure onsets within 24 hours after administration of the pharmaceutical composition. In another embodiment, the ketamine pamoate salts of the present disclosure exhibit a therapeutic effect lasting for at least 24 hours, at least two days, at least one week, at least ten days, or at least two weeks.

Different examples have been used to illustrate the present disclosure. The examples below should not be taken as a limit to the scope of the present disclosure.

EXAMPLES

Example 1. Preparation of S- and R-Enantiomers of Ketamine Pamoate

The preparation flow of S-ketamine pamoate and R-ketamine pamoate was shown as Scheme 1 below.

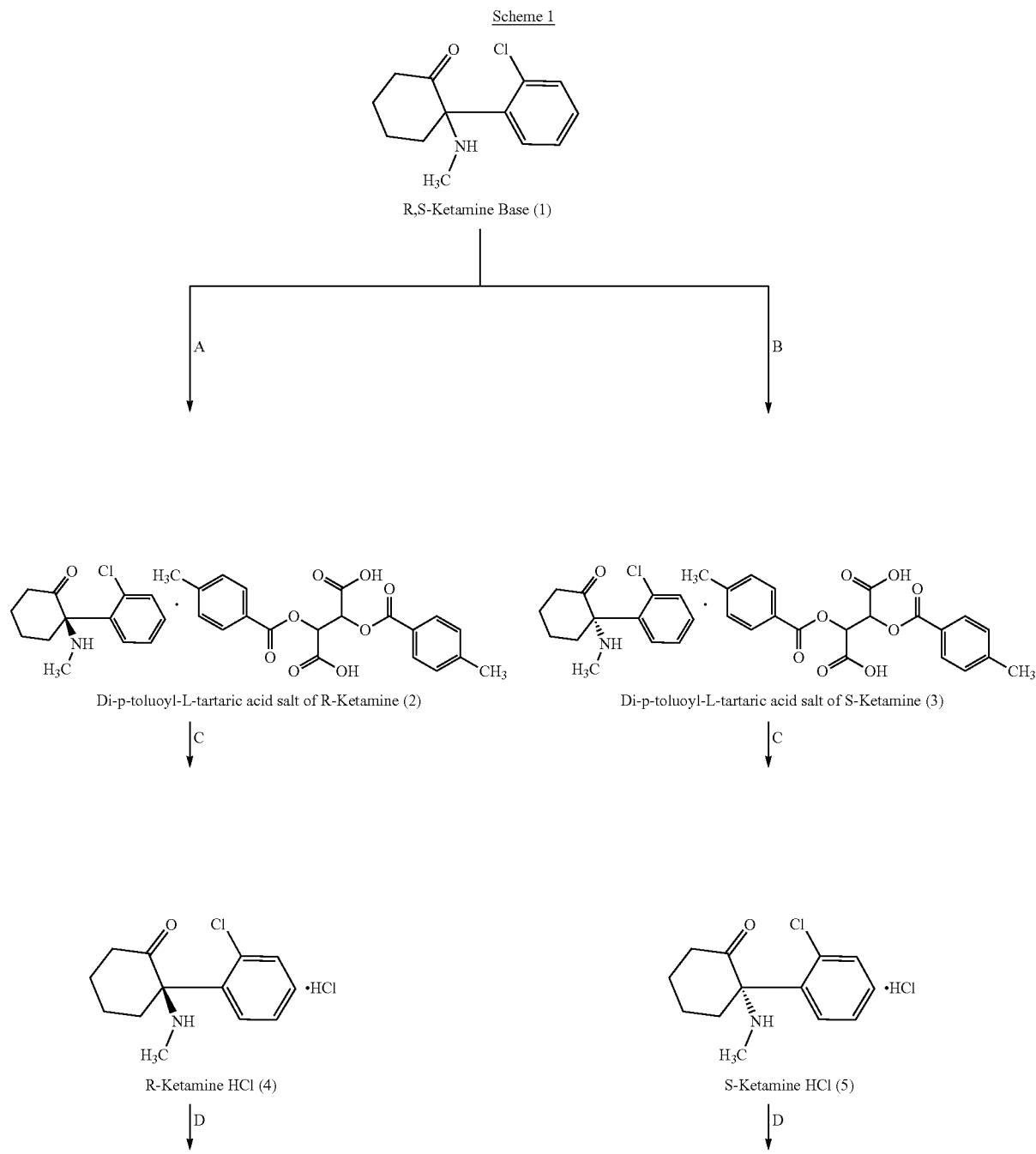

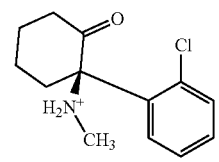
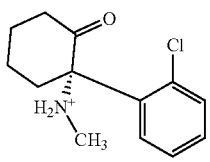

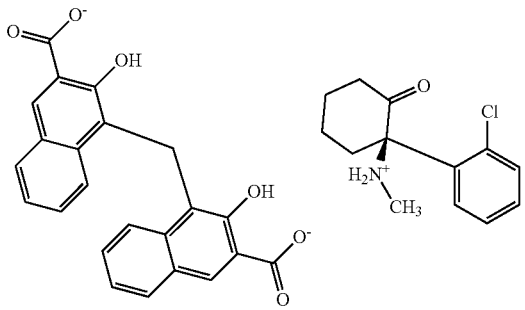
R-Ketamine pamoate salt (6)

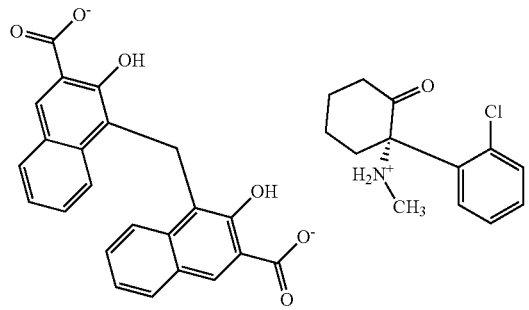
S-Ketamine pamoate salt (7)

A: Di-p-toluoyl-L-tartaric acid/EtOH, EtOH/H$_2$O(3:2)
B: Di-p-toluoyl-L-tartaric acid/EtOH, EtOH/H$_2$O(2:3)
C: HCl/THF
D: Disodium pamoate/H$_2$O

Example 1-1. Preparation of R, S-Ketamine Free Base (1)

10 g of R, S-ketamine hydrochloride was dissolved in 100 mL of water, and then 150 mL of saturated sodium bicarbonate aqueous solution was added with stirring for 10 min. The reaction mixture was extracted with dichloromethane (100 mL×2). The separated organic layers were combined and distilled under reduced pressure to get R, S-ketamine free base (1).

Example 1-2. Preparation of (−)-O, O'-Di-p-Toluoyl-L-Tartaric Acid Salt of R-Ketamine (2)

Di-p-toluoyl-L-tartaric acid (13 g, 33.6 mmol) and R, S-ketamine free base (8 g, 33.6 mmol) were dissolved in ethanol (EtOH, 160 mL) with stirring for 5 min. 10 mL water was added dropwise to the solution at room temperature, followed by stirring for 1 hr to obtain a precipitate. The filtrate solution was collected after suction filtration and dried under vacuum. The residue was dissolved in 100 mL of 60% ethanol solution (i.e., EtOH:H$_2$O=3:2) at 60° C., and cooled to room temperature for 1 hr to obtain the solid, followed by drying under vacuum.

The resulting powder was analyzed by high-performance liquid chromatography (HPLC), differential scanning calorimetry (DSC), optical rotation, nuclear magnetic resonance (NMR) spectrum, and literature information. The characterization of (−)-O, O'-Di-p-toluoyl-L-tartaric acid salt of R-ketamine (2) was confirmed by specific rotation, melting point (m.p.), and HPLC chiral purity as shown below:

m.p.=133.5-141.3° C., $[\alpha]_D^{25°}$=−75°, c=1.0, dimethyl formamide, chiral purity=98.4%. $^1$H-NMR (DMSO-d$_6$): 7.87 (d, 4H, J=8.0 Hz), 7.68 (d, 1H, J=6.8 Hz), 7.44 (m, 3H), 7.36 (d, 4H, J=8.0 Hz), 5.74 (s, 2H), 2.66-2.32 (m, 2H), 2.39 (s, 6H), 2.04 (s, 3H), 1.90-1.58 (m, 6H).

Example 1-3. Preparation of (−)-O, O'-Di-p-Toluoyl-L-Tartaric Acid Salt of S-Ketamine (3)

The precipitate from Example 1-2 was dried under reduced pressure. The solid was dissolved in 100 mL of 40% ethanol solution (i.e., EtOH:H$_2$O=2:3) at 60° C., and cooled to room temperature for 1 hr to obtain the solid, followed by drying under vacuum.

The resulting powder was analyzed by HPLC, DSC, optical rotation, NMR spectrum, and literature information. The characterization of (−)-O, O'-Di-p-toluoyl-L-tartaric acid salt of S-ketamine (3) was confirmed by specific rotation, melting point (m.p.), and HPLC chiral purity as shown below:

m.p.=157.1-163.3° C., $[\alpha]_D^{25°}$=−108°, c=1.0, dimethyl formamide, chiral purity=100%. $^1$H-NMR (DMSO-d$_6$): 7.87 (d, 4H, J=7.6 Hz), 7.67 (d, 1H, J=7.6 Hz), 7.44 (m, 3H), 7.36 (d, 4H, J=8.0 Hz), 5.74 (s, 2H), 2.64-2.31 (m, 2H), 2.39 (s, 6H), 2.03 (s, 3H), 1.91-1.59 (m, 6H).

Example 1-4. Preparation of R-Ketamine Pamoate (6) (Crystal)

Di-p-toluoyl-L-tartaric acid salt of R-ketamine (2) was dissolved in ten-fold tetrahydrofuran (THF) by stirring at 2° C. to 10° C. Hydrochloride (37%) was added to the solution to obtain a precipitate, and the precipitate was collected by suction filtration to obtain R-ketamine hydrochloride (4). R-ketamine hydrochloride (4) and disodium pamoate were dissolved separately in ten-fold water. Afterwards, water was distilled from the reaction mixture by decompression. The residue was dissolved in ethanol stirring at 60° C. and recrystallized by decreasing temperature.

The resulting powder was analyzed by HPLC, DSC, infrared (IR), X-ray diffraction pattern (XRD), and NMR spectrums. The characterization of the crystal form of R-ketamine pamoate (6) was confirmed by analysis results and specific rotation of R-ketamine pamoate (6) of $[\alpha]_D^{25°}$=+67°.

Example 1-5. Preparation of S-Ketamine Pamoate (7) (Crystal)

Di-p-toluoyl-L-tartaric acid salt of S-ketamine (3) was dissolved in ten-fold tetrahydrofuran (THF) by stirring at 2°

C. to 10° C. Hydrochloride (37%) was added to the solution to obtain a precipitate, and the precipitate was collected by suction filtration to obtain S-ketamine hydrochloride (5). S-ketamine hydrochloride (5) and disodium pamoate were dissolved separately in ten-fold water. Afterwards, water was distilled from the reaction mixture by decompression. The residue was recrystallized with ethanol stirring at 60° C. and isolated by vacuum filtration.

The resulting powder was analyzed by HPLC, DSC, optical rotation, IR, XRD, and NMR spectrums. The characterization of the crystal form of S-ketamine pamoate (7) was confirmed by analysis results and specific rotation of S-ketamine pamoate (7) of $[\alpha]_D^{25°}=-67°$.

Example 1-6. Preparation of R-Ketamine Pamoate (Amorphous)

R-ketamine pamoate (6) was dissolved in methanol, and the solvent was removed under reduced pressure to get the amorphous form of R-ketamine pamoate.

The resulting powder was analyzed by HPLC, DSC, optical rotation, IR, XRD, and NMR spectrums. The characterization of the amorphous form of R-ketamine pamoate was confirmed by analysis results and specific rotation of R-ketamine pamoate of $[\alpha]_D^{25°}=+67°$.

Example 1-7. Preparation of S-Ketamine Pamoate Salt (Amorphous)

S-ketamine pamoate (7) was dissolved in methanol, and the solvent was removed under reduced pressure to get the amorphous form of S-ketamine pamoate.

The resulting powder was analyzed by HPLC, DSC, optical rotation, IR, XRD, and NMR spectrums. The characterization of the amorphous form of S-ketamine pamoate was confirmed by analysis results and specific rotation of S-ketamine pamoate of $[\alpha]_D^{25°}=-67°$.

Example 1-8. Preparation of R, S-Ketamine Pamoate (Crystal)

Ketamine HCl and deionized water were added to form a solution, which was added dropwise to a disodium pamoate monohydrate aqueous solution with stirring in a round-bottom flask. The mixture was stirred constantly at room temperature for 1 hour. This reaction mixture was filtered, and the powder was collected and dried under reduced pressure. The resulting powder was analyzed by HPLC, DSC, IR, XRD, and NMR spectrums.

Example 1-9. Preparation of R, S-Ketamine Pamoate (Amorphous)

The powders collected from Example 1-8 was dissolved in methanol. Further, the solvent was removed under reduced pressure and dried to get the amorphous form of R, S-ketamine pamoate. The resulting powder was analyzed by HPLC, DSC, IR, XRD, and NMR spectrums.

Example 2. Characterization of Ketamine Pamoate

Figure 1A:
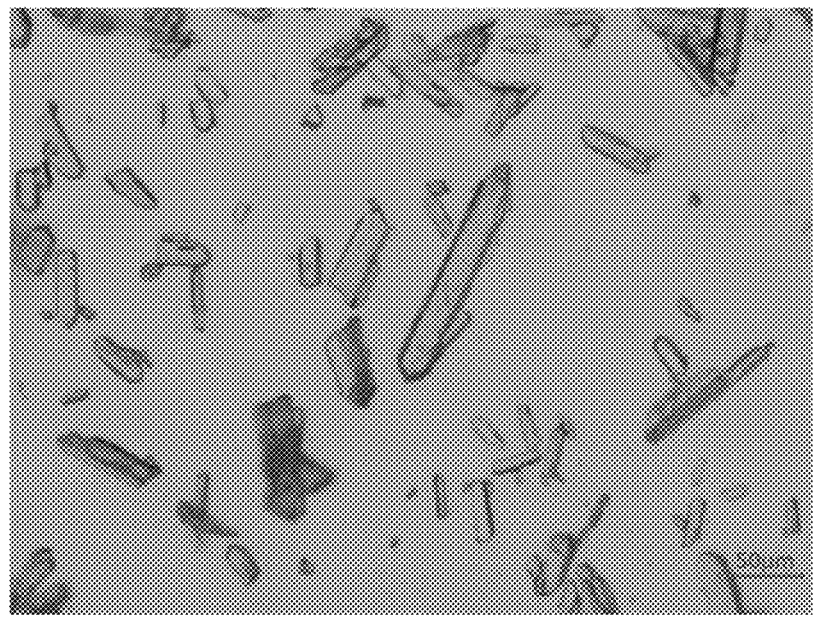
FIGS. 1A and 1B illustrate microscope images of crystalline and amorphous of R, S-ketamine pamoate salts, respectively.
Figure 1B:
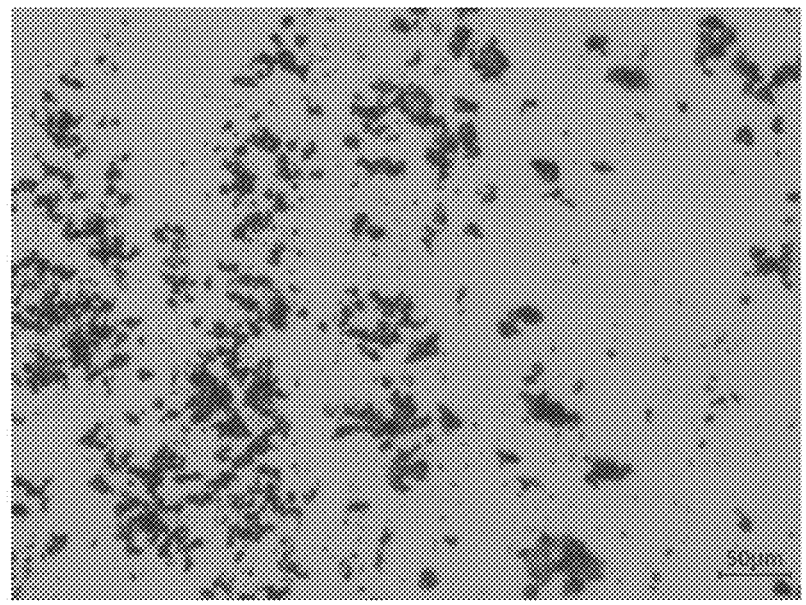

The pamoate salt of ketamine pamoate obtained from Example 1 was crystalline or amorphous. By Olympus CX41 polarizing microscope, such dense crystal and non-crystal powders were shown in FIGS. 1A and 1B, respectively.

Further, the characterizations of R, S-ketamine pamoate, S-ketamine pamoate, and R-ketamine pamoate in amorphous or crystal form were analyzed by HPLC, DSC, IR, XRD, and NMR spectrums. The processes of such analyses and the characterizations of ketamine pamoate were described in detail as follows.

Example 2-1. XRPD Analysis

The X-ray powder diffraction (XRPD) pattern was obtained on a Bruker D Discover X-ray powder diffractometer, equipped with a CuKα radiation source of wavelength (λ=1.54056 Å), operating at 40 kV and 40 mA.

Each sample was scanned between 22 and 800 in 2θ, with a step size of 0.02° in 2θ and a scan rate of 0.6 second/step. The angular peak positions in 2θ and corresponding $I/I_o$ data for all crystal forms of ketamine pamoate peaks with intensities equal to or greater than 10% of the largest peak were tabulated in Table 1 below.

Crystal forms and amorphous forms of salts of S-ketamine pamoate, R-ketamine pamoate, and R, S-ketamine pamoate were characterized by XRD, and the results were provided in FIGS. 2A to 2F.

TABLE 1

| X-ray diffraction peaks of crystal forms of R,S-ketamine pamoate, S-ketamine pamoate, and R-ketamine pamoate ||||||||
|---|---|---|---|---|---|---|---|
| R,S-ketamine pamoate ||| S-ketamine pamoate ||| R-ketamine pamoate ||
| 2θ [deg.] | d-spacing | $I/I_o$ | 2θ [deg.] | d-spacing | $I/I_o$ | 2θ [deg.] | d-spacing | $I/I_o$ |
| 6.0 | 14.70 | 10.1 | 6.0 | 14.72 | 13.7 | 6.0 | 14.75 | 14.3 |
| 8.6 | 10.32 | 14.7 | — | — | — | — | — | — |
| 10.7 | 8.26 | 22.7 | 10.8 | 8.19 | 19.3 | 10.8 | 8.19 | 25.0 |
| 11.6 | 7.64 | 32.1 | 11.7 | 7.56 | 36.1 | 11.7 | 7.56 | 46.4 |
| 12.0 | 7.34 | 100.0 | 12.0 | 7.35 | 34.0 | 12.0 | 7.35 | 39.8 |
| — | — | — | 12.6 | 7.01 | 12.1 | 12.6 | 7.01 | 15.9 |
| 13.0 | 6.79 | 80.1 | 13.1 | 6.76 | 38.8 | 13.1 | 6.77 | 46.9 |
| 14.7 | 6.01 | 50.0 | 14.6 | 6.08 | 16.5 | 14.6 | 6.07 | 19.3 |
| 15.0 | 5.91 | 59.0 | 15.1 | 5.87 | 26.7 | 15.0 | 5.89 | 33.4 |
| 15.3 | 5.75 | 11.6 | — | — | — | — | — | — |
| 17.9 | 4.96 | 63.0 | — | — | — | — | — | — |
| — | — | — | 18.2 | 4.87 | 48.9 | 18.2 | 4.86 | 57.0 |
| 18.6 | 4.77 | 40.0 | — | — | — | — | — | — |
| — | — | — | 19.2 | 4.61 | 32.7 | 19.3 | 4.60 | 38.4 |
| 19.6 | 4.53 | 40.4 | 19.7 | 4.50 | 22.4 | 19.7 | 4.50 | 28.2 |
| 20.0 | 4.43 | 28.0 | 20.1 | 4.41 | 12.4 | 20.6 | 4.31 | 10.8 |

TABLE 1-continued

X-ray diffraction peaks of crystal forms of R,S-ketamine pamoate, S-ketamine pamoate, and R-ketamine pamoate

| R,S-ketamine pamoate | | | S-ketamine pamoate | | | R-ketamine pamoate | | |
|---|---|---|---|---|---|---|---|---|
| 2θ [deg.] | d-spacing | I/I$_o$ | 2θ [deg.] | d-spacing | I/I$_o$ | 2θ [deg.] | d-spacing | I/I$_o$ |
| 21.1 | 4.22 | 14.1 | — | — | — | — | — | — |
| 21.6 | 4.11 | 28.6 | — | — | — | — | — | — |
| 22.2 | 4.00 | 15.1 | 22.0 | 4.04 | 15.6 | 22.0 | 4.04 | 19.7 |
| — | — | — | 22.8 | 3.89 | 21.0 | 22.9 | 3.89 | 25.4 |
| 23.3 | 3.81 | 46.5 | 23.3 | 3.81 | 16.4 | 23.6 | 3.76 | 22.0 |
| — | — | — | 23.7 | 3.76 | 18.1 | 24.1 | 3.69 | 20.4 |
| 24.4 | 3.65 | 37.3 | 24.1 | 3.69 | 15.8 | — | — | — |
| — | — | — | 24.7 | 3.60 | 12.3 | 24.7 | 3.60 | 17.1 |
| 25.2 | 3.54 | 26.8 | 25.2 | 3.53 | 13.6 | 25.2 | 3.53 | 16.9 |
| 25.9 | 3.42 | 14.7 | — | — | — | 25.9 | 3.43 | 13.6 |
| 26.9 | 3.31 | 20.0 | — | — | — | — | — | — |
| — | — | — | 27.3 | 3.27 | 13.2 | 27.3 | 3.26 | 19.3 |
| 28.6 | 3.11 | 16.0 | — | — | — | — | — | — |
| 29.7 | 3.00 | 16.1 | — | — | — | — | — | — |
| 30.3 | 2.95 | 20.7 | 30.1 | 2.97 | 11.9 | 30.1 | 2.97 | 14.9 |
| — | — | — | 31.6 | 2.83 | 100.0 | 31.6 | 2.83 | 100.0 |
| 32.4 | 2.76 | 11.6 | — | — | — | — | — | — |
| 34.0 | 2.64 | 18.6 | — | — | — | — | — | — |
| 36.6 | 2.45 | 10.8 | — | — | — | — | — | — |
| — | — | — | 45.4 | 2.00 | 49.4 | 45.4 | 2.00 | 54.2 |
| — | — | — | 56.4 | 1.63 | 10.6 | 56.4 | 1.63 | 16.6 |
| — | — | — | 75.2 | 1.26 | 12.3 | 75.2 | 1.26 | 12.2 |

Example 2-2. NMR Analysis

The salts of R, S-ketamine pamoate, S-ketamine pamoate, and R-ketamine pamoate were dissolved in a deuterium solvent (DMSO), and NMR spectra were obtained using a Bruker Ascend TM 400 MHz NMR spectrometer.

Figure 3A:
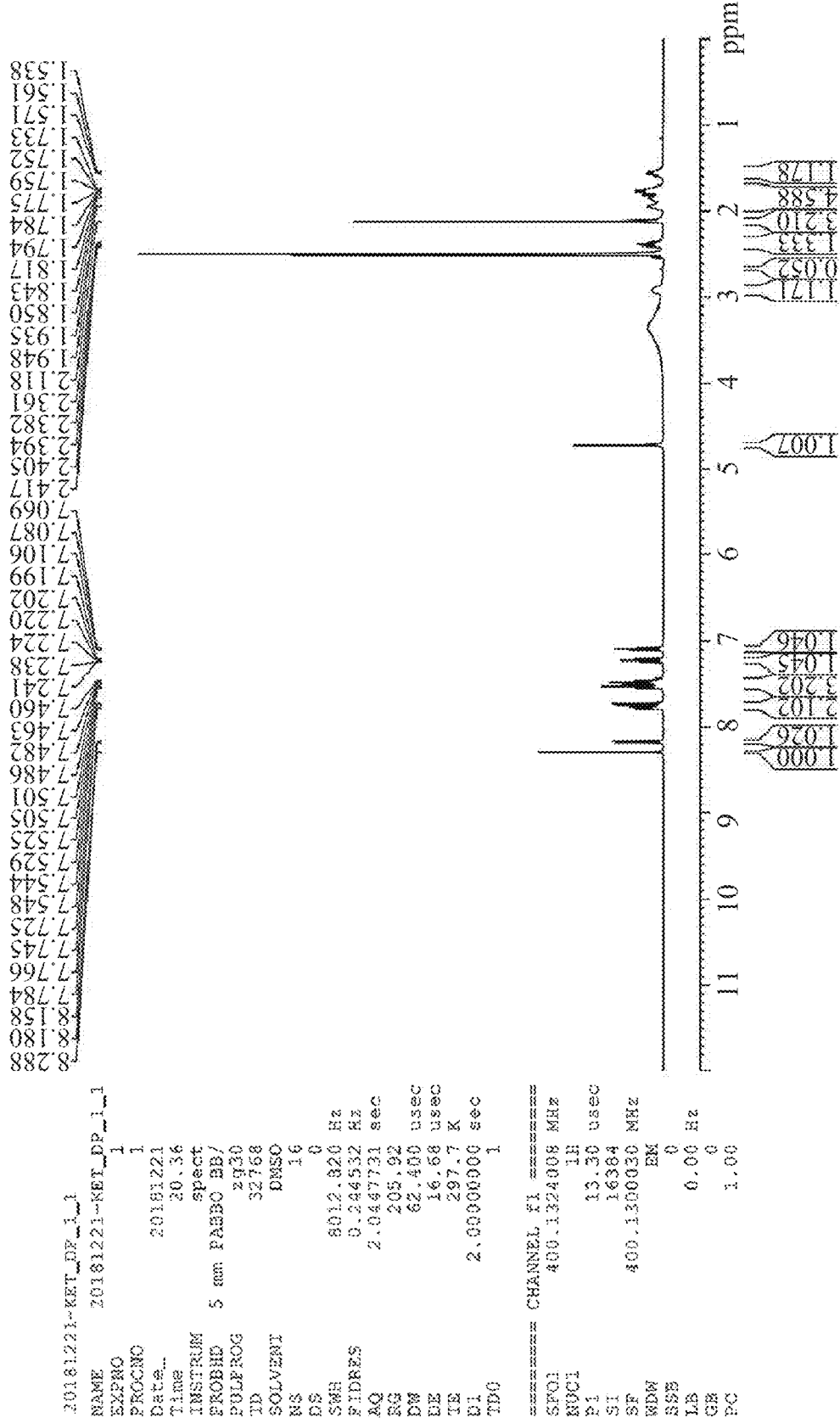
FIGS. 3A to 3C illustrate the $^1$H nuclear magnetic resonance spectrums of R, S-ketamine pamoate, S-ketamine pamoate, and R-ketamine pamoate in crystal form, respectively.
Figure 3B:
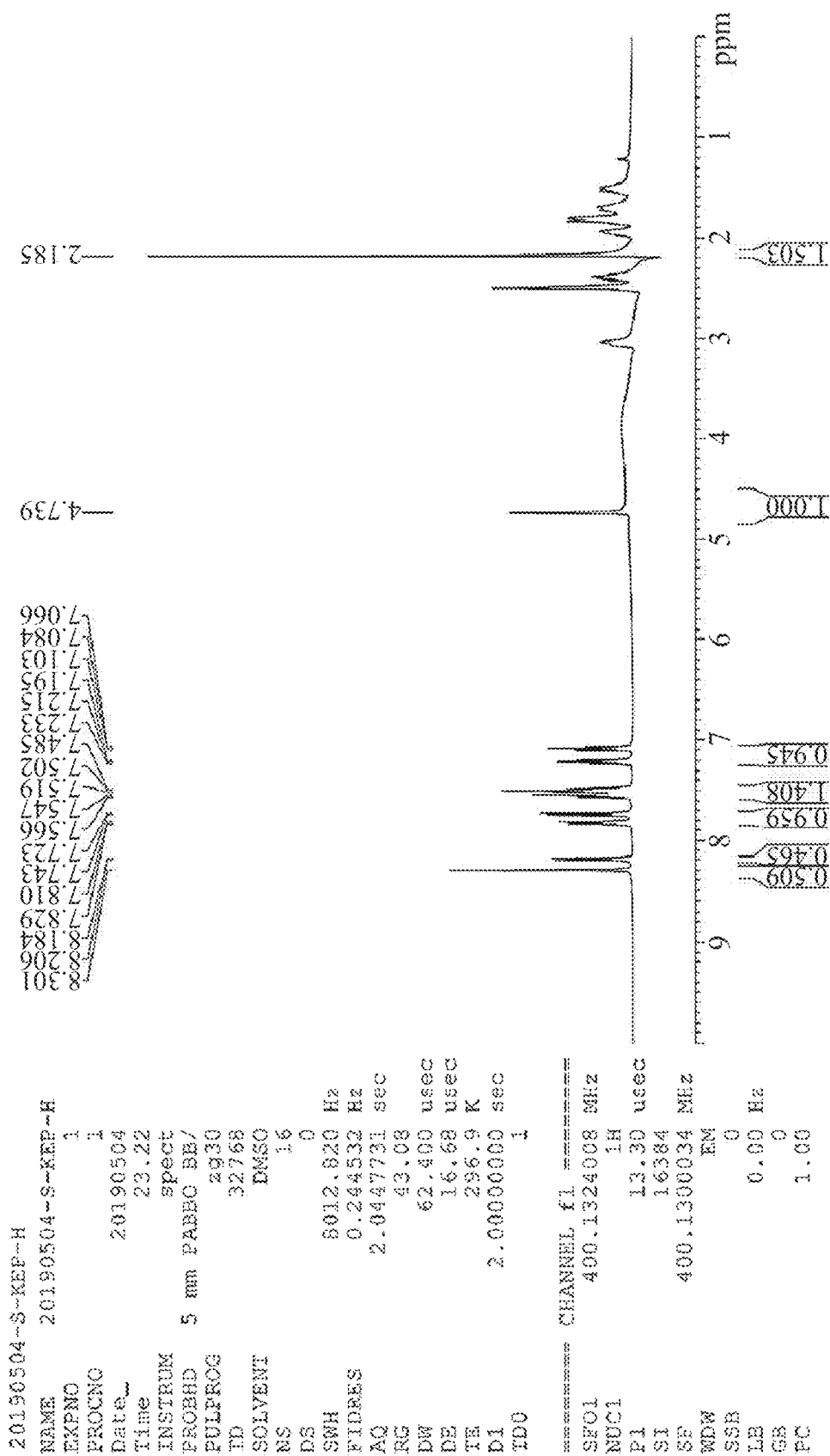
Figure 3C:
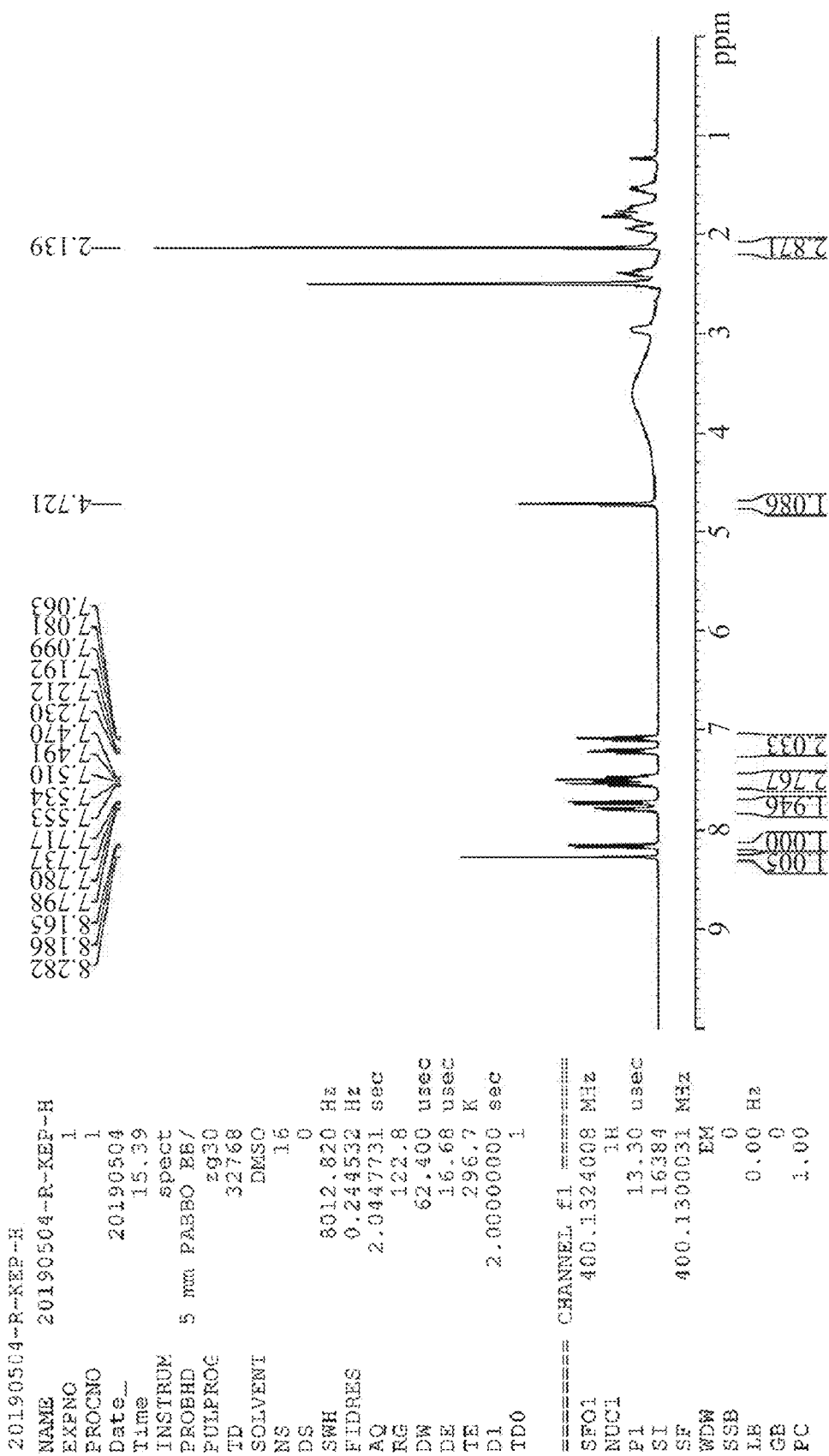
Figure 4A:
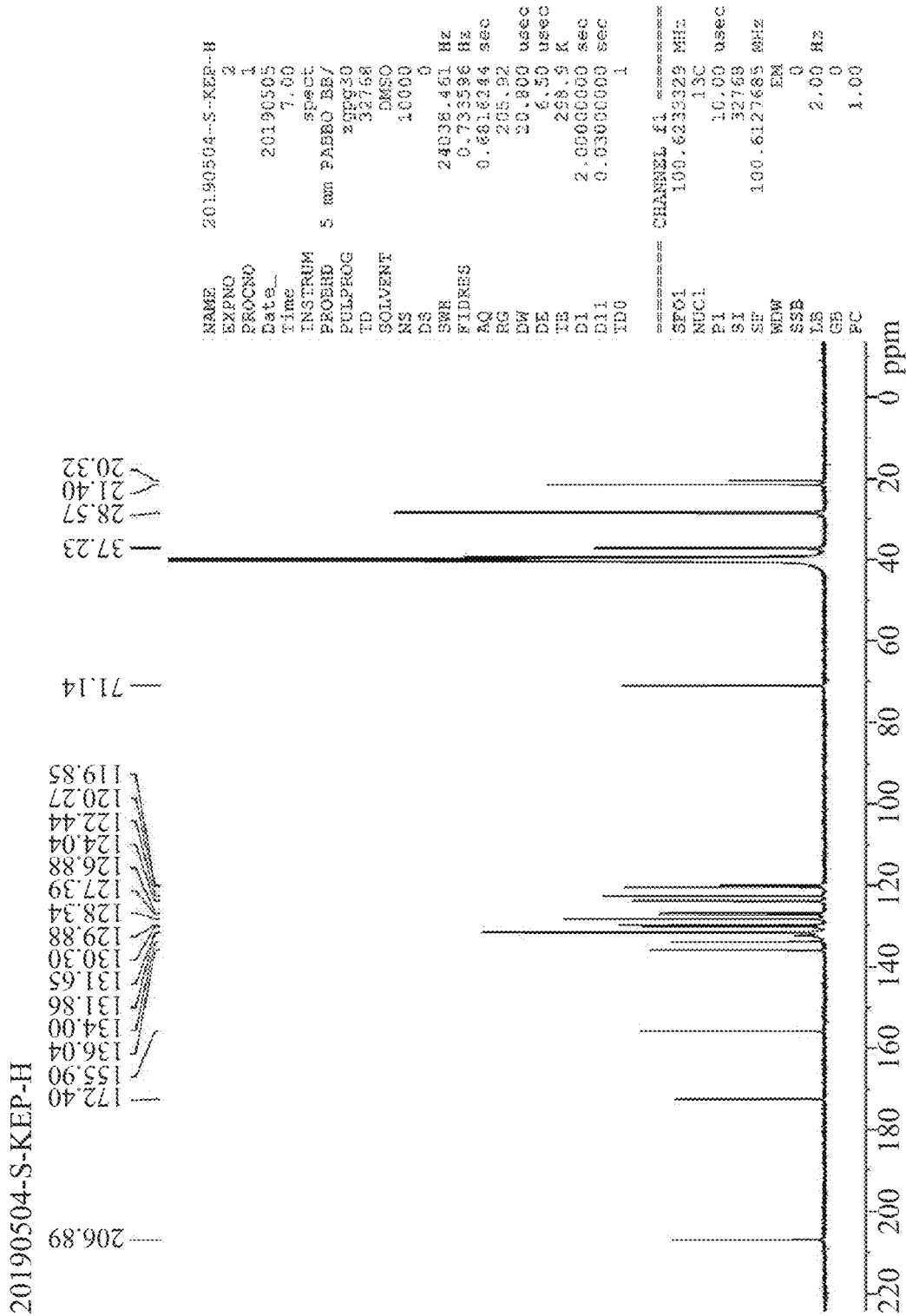
FIGS. 4A and 4B illustrate the $^{13}$C nuclear magnetic resonance spectrums of S-ketamine pamoate and R-ketamine pamoate in crystal form, respectively.
Figure 4B:
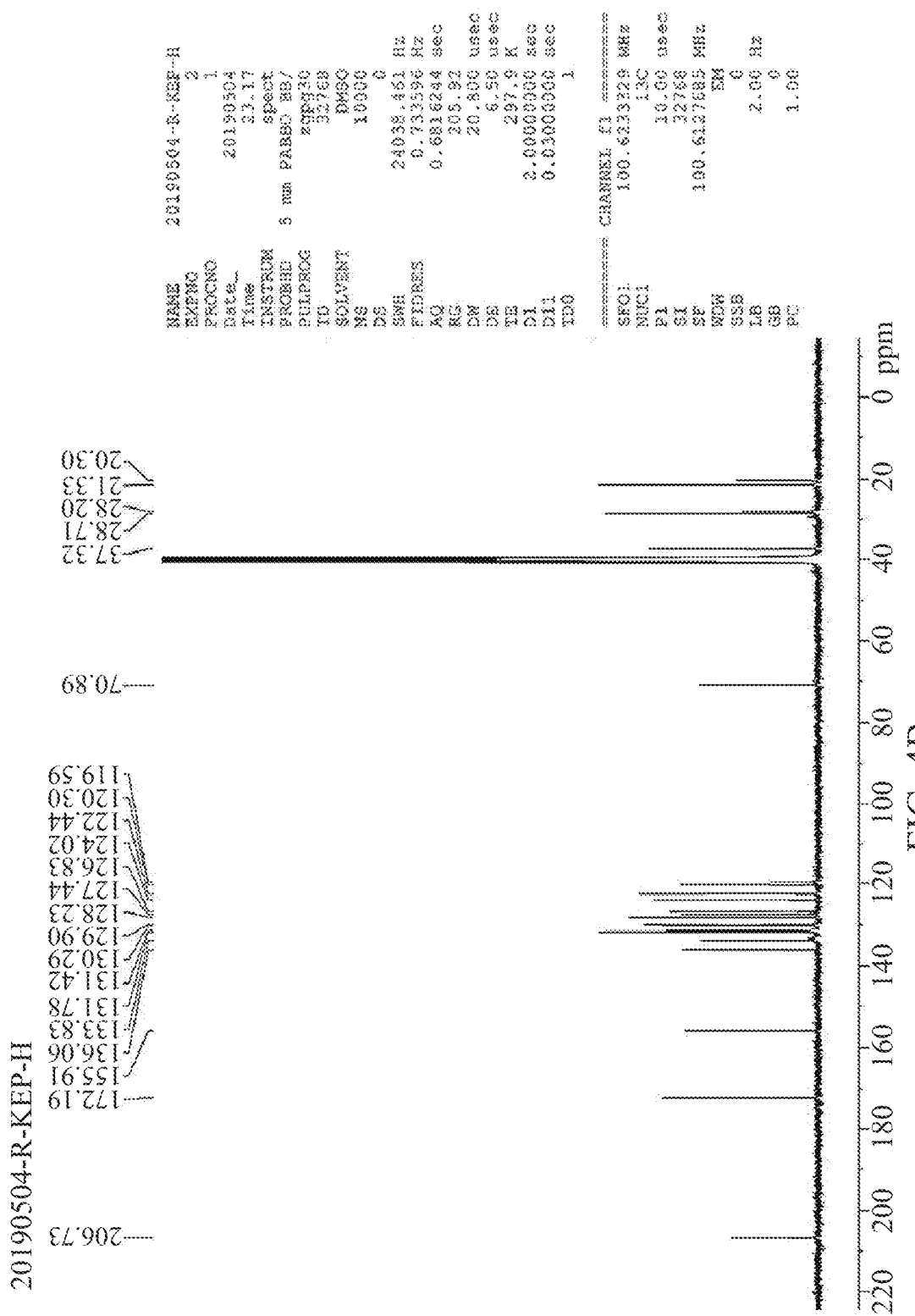
Figure 5A:
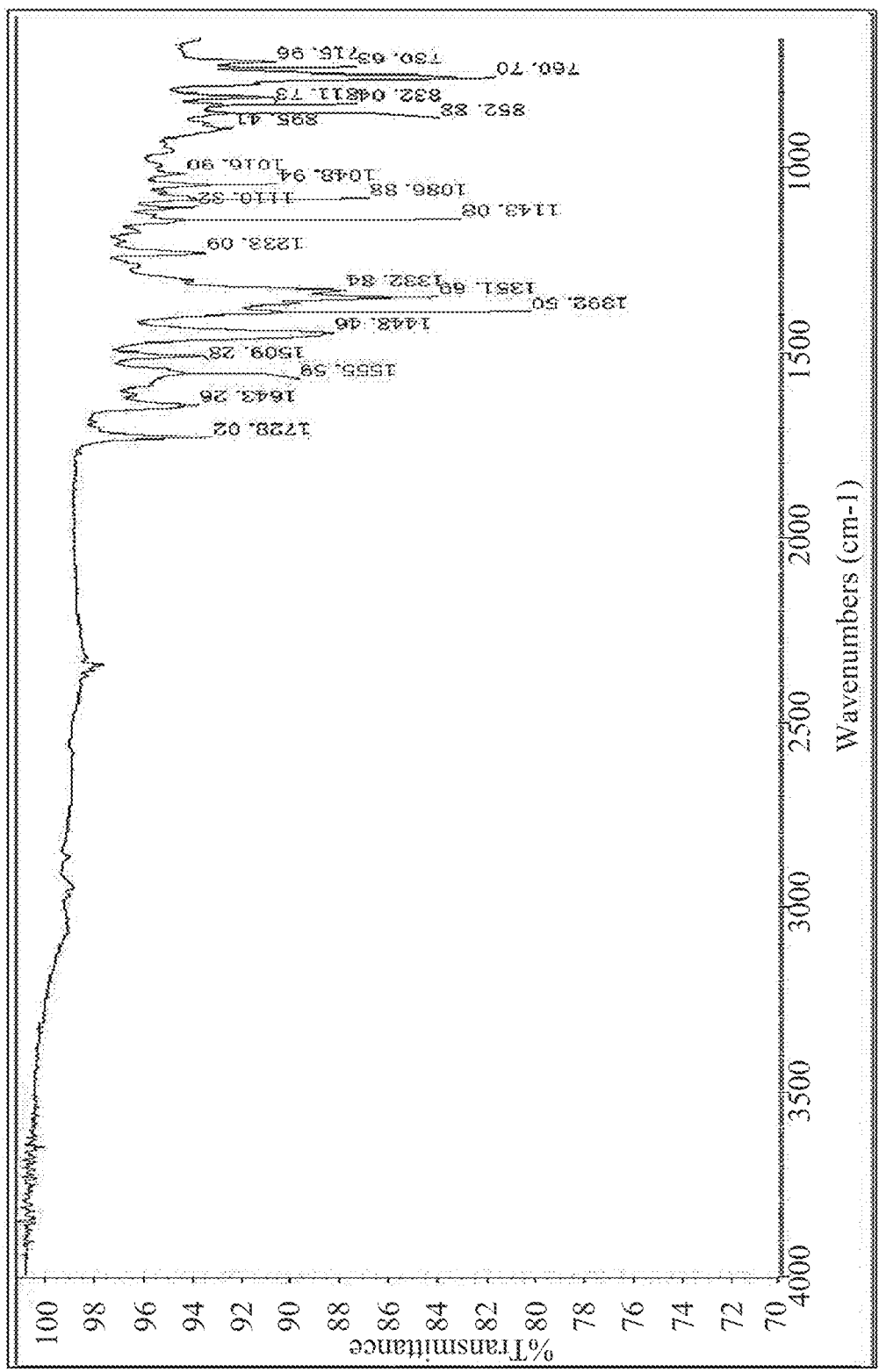
FIGS. 5A to 5E illustrate the Fourier-transform (FT) infrared spectrum of S-ketamine pamoate and R-ketamine pamoate in crystal form (FIGS. 5A and 5B) or amorphous form (FIGS. 5C and 5D), and R, S-ketamine pamoate in amorphous form (FIG. 5E), respectively.
Figure 5B:
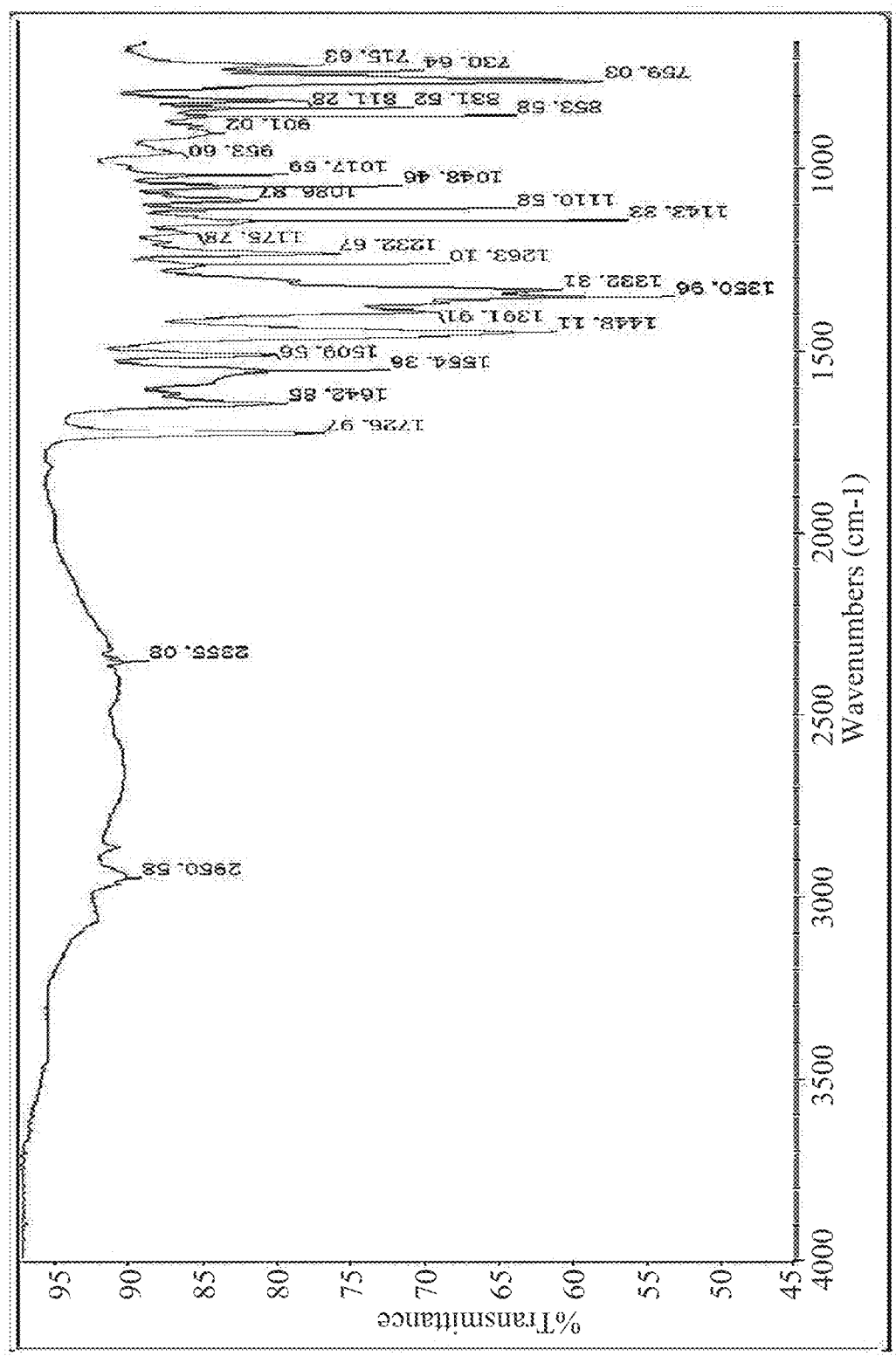
Figure 5C:
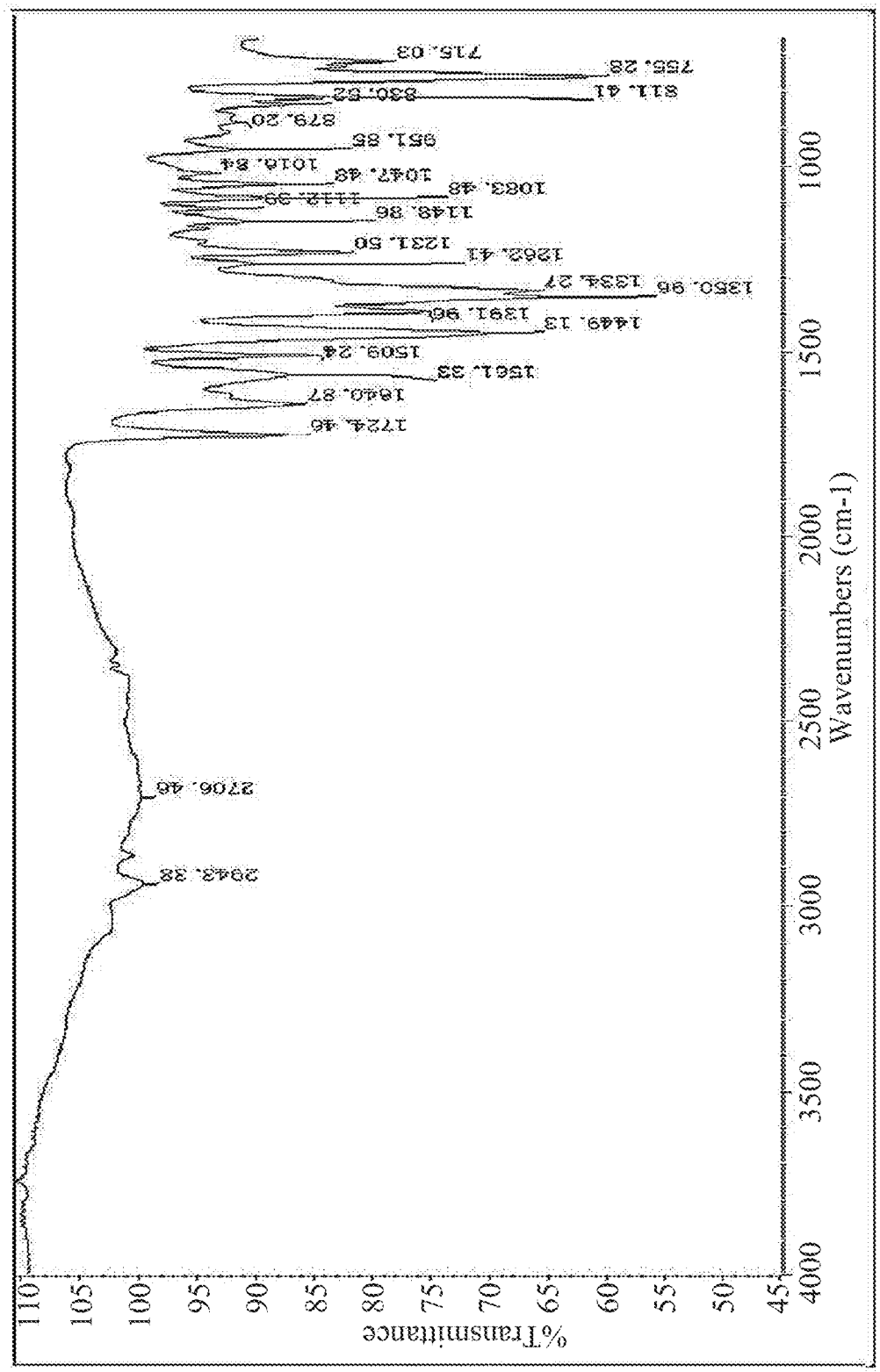
Figure 5D:
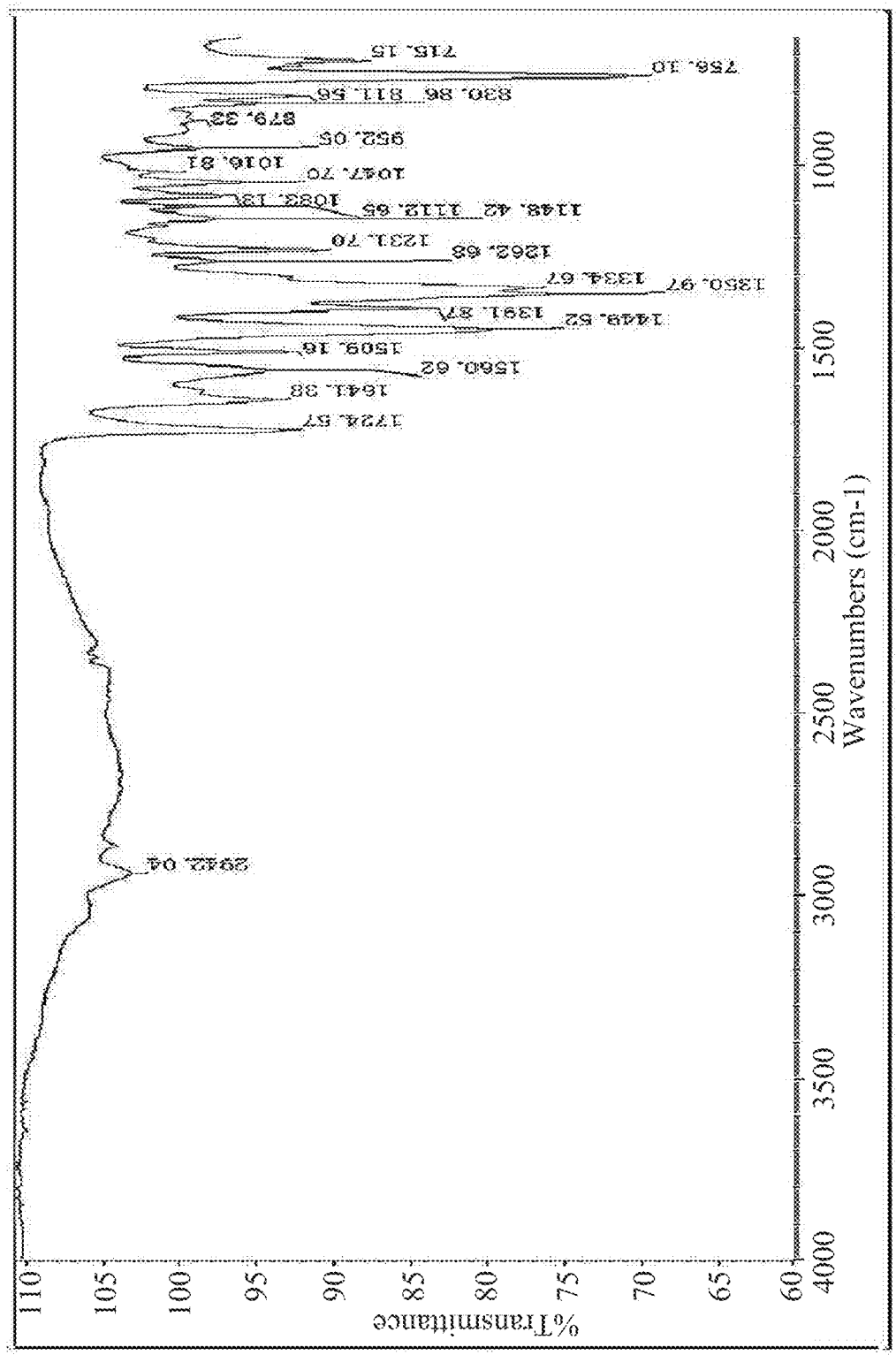
Figure 5E:
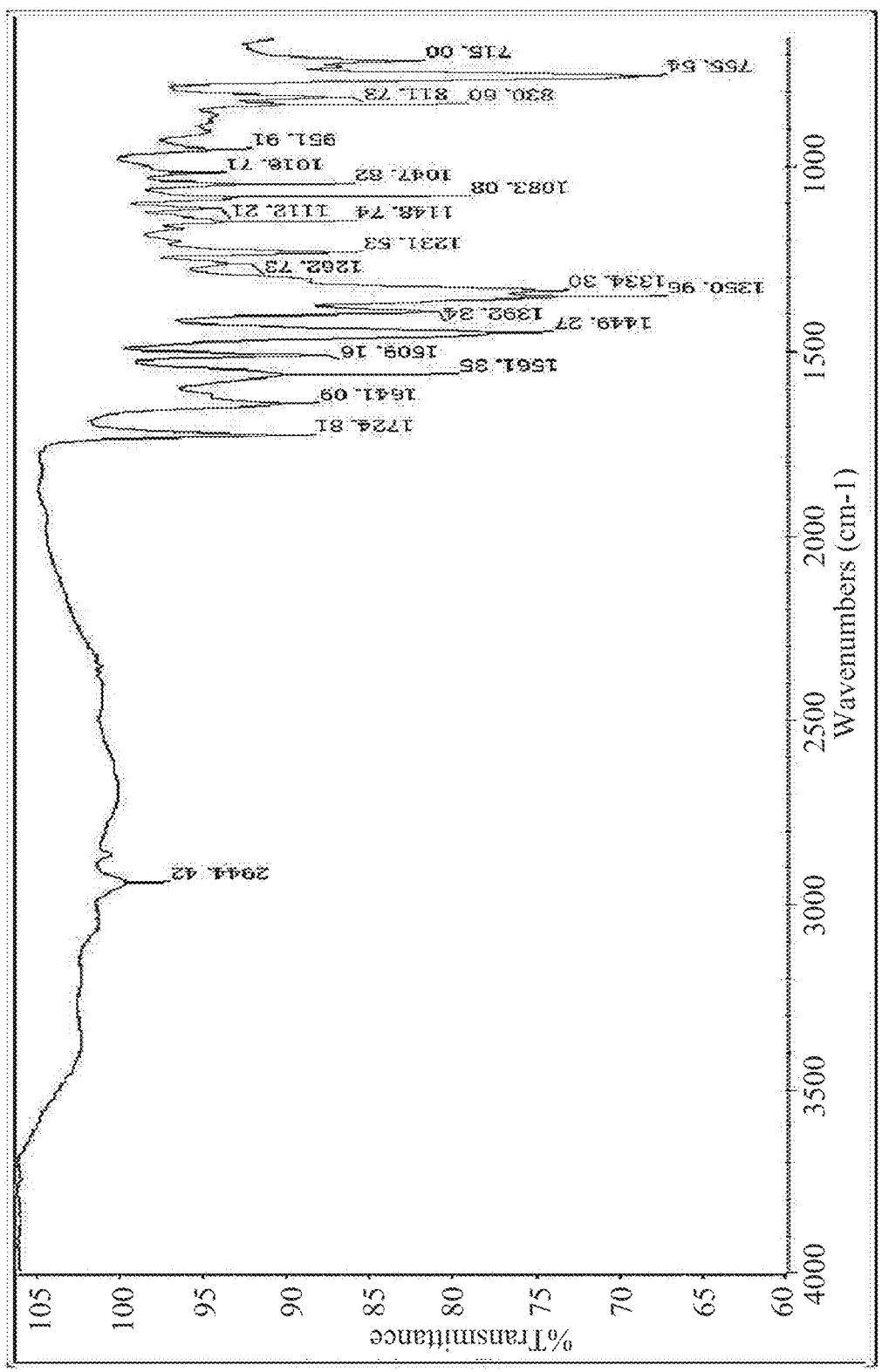

The characterizations of the salts of R, S-ketamine pamoate, S-ketamine pamoate, and R-ketamine pamoate were confirmed by $^1$H-NMR spectroscopy (as illustrated in Table 2 and FIGS. 3A to 3C). Further, S-ketamine pamoate and R-ketamine pamoate were subjected to $^{13}$C-NMR spectroscopy, and chemical shifts were reported in ppm (as illustrated in Table 3 and FIGS. 4A and 4B).

TABLE 2

$^1$H-NMR (400 MHz, DMSO) data of R, S-ketamine pamoate, S-ketamine pamoate, and R-ketamine pamoate

| Compound | R, S-ketamine pamoate (Crystal) | S-ketamine pamoatae (Crystal) | R-ketamine pamoate (Crystal) |
|---|---|---|---|
| Chemical shift (δ ppm) | 1.96-1.57 (m, 12H) | 1.95-1.51 (m, 12H) | 1.97-1.53 (m, 12H) |
| | 2.12 (s, 6H) | 2.19 (s, 6H) | 2.15 (s, 6H) |
| | 2.51-2.34 (m, 4H) | 2.51-2.34 (m, 4H) | 2.50-2.37 (m, 4H) |
| | 4.72 (s, 2H) | 4.74 (s, 2H) | 4.72 (s, 2H) |
| | 7.09 (dd, 2H, J = 14.8 Hz, 7.2 Hz) | 7.08 (dd, 2H, J = 14.8 Hz, 7.2 Hz) | 7.08 (dd, 2H, J = 14.8 Hz, 7.2 Hz) |
| | 7.21 (dd, 2H, J = 8.4 Hz, 1.2 Hz) | 7.21 (dd, 2H, J = 15.2 Hz, 7.2 Hz) | 7.21 (dd, 2H, J = 15.2 Hz, 7.2 Hz) |
| | 7.51 (m, 6H) | 7.52 (m, 6H) | 7.52 (m, 6H) |
| | 7.75 (dd, 4H, J = 16.4 Hz, 8 Hz) | 7.82 (d, 2H, J =7.6 Hz), 7.73 (d, 2H, J = 8 Hz) | 7.79 (d, 2H, J = 7.2 Hz), 7.73 (d, 2H, J = 8.0 Hz) |
| | 8.17 (d, 2H, J = 8.8 Hz) | 8.19 (d, 2H, J =8.8 Hz) | 8.17 (d, 2H, J = 8.4 Hz) |
| | 8.29 (s, 2H) | 8.30 (s, 2H) | 8.28 (s, 2H) |

TABLE 3

$^{13}$C-NMR (100 MHz, DMSO) data of S-ketamine pamoate and R-ketamine pamoate

| Compound | S-ketamine pamoate (Crystal) | R-ketamine pamoate (Crystal) | Number of carbons | Assignment |
|---|---|---|---|---|
| Chemical shift (δ ppm) | 20.3 | 20.3 | 1C | Ph—CH$_2$—Ph |
| | 21.4 | 21.3 | 2C | —CH$_2$— |
| | 28.6 | 28.7 | 6C | —CH$_2$— |
| | 37.2 | 37.3 | 2C | N—CH$_3$ |
| | 71.1 | 70.9 | 2C | >C—N |
| | 119.8 | 119.6 | 2C | Aromatic, =C< |
| | 120.3 | 120.3 | 2C | Aromatic, =CH— |
| | 122.4 | 122.4 | 2C | Aromatic, =CH— |
| | 124.0 | 124.0 | 2C | Aromatic, =CH— |
| | 126.9 | 126.8 | 2C | Aromatic, =C< |
| | 127.4 | 127.4 | 2C | Aromatic, =CH— |
| | 128.3 | 128.2 | 2C | Aromatic, =C< |
| | 129.9 | 129.9 | 2C | Aromatic, =C< |
| | 130.3 | 130.3 | 2C | Aromatic, =CH— |
| | 131.7 | 131.4 | 4C | Aromatic, =CH— |
| | 131.9 | 131.8 | 4C | Aromatic, =CH— |
| | 134.0 | 133.8 | 2C | Aromatic, =C< |
| | 136.0 | 136.1 | 2C | Aromatic, =C—OH |
| | 155.9 | 155.9 | 2C | Aromatic, =C—Cl |
| | 172.4 | 172.2 | 2C | O—C=O |
| | 206.9 | 206.7 | 2C | >C=O |

Example 2-3. Fourier-Transform Infrared (FT-IR) Spectroscopy Analysis

The polymorphs of ketamine pamoate were further characterized by infrared (IR) spectroscopy obtained in a disk using a Bruker FPA-FTIR Vertex 70V, Hyperion 3000 system, and the results were shown in FIGS. 5A to 5E. The IR absorbances (in wavenumbers, cm$^{-1}$) sufficient to identify crystalline and amorphous forms of S-, R-enantiomers of ketamine pamoate were reported in Table 4 below.

TABLE 4

FT-IR peaks of S-ketamine pamoate, R-ketamine pamoate and R, S-ketamine pamoate

| S-ketamine pamoate (Crystal) cm$^{-1}$ | S-ketamine pamoate (Crystal) cm$^{-1}$ | S-ketamine pamoate (Amorphous) cm$^{-1}$ | R-ketamine pamoate (Amorphous) cm$^{-1}$ | R, S-ketamine pamoate (Amorphous) cm$^{-1}$ |
|---|---|---|---|---|
| 716 | 716 | 715 | 715 | 715 |
| 731 | 730 | — | — | — |
| 760 | 759 | 755 | 756 | 755 |
| 812 | 811 | 811 | 812 | 812 |
| 832 | 832 | 831 | 831 | 831 |
| 853 | 854 | — | — | — |
| 895 | 901 | — | — | — |
| 1049 | 1048 | 1048 | 1048 | 1048 |
| 1087 | 1087 | 1084 | 1083 | 1083 |
| 1143 | 1143 | 1149 | 1148 | 1148 |
| 1233 | 1233 | 1232 | 1232 | 1232 |
| 1333 | 1332 | 1334 | 1335 | 1334 |
| 1352 | 1351 | 1351 | 1351 | 1351 |
| 1393 | 1392 | 1392 | 1392 | 1392 |
| 1448 | 1448 | 1449 | 1450 | 1449 |
| 1509 | 1510 | 1509 | 1509 | 1509 |
| 1556 | 1554 | 1561 | 1561 | 1561 |
| 1643 | 1643 | 1641 | 1641 | 1641 |
| 1728 | 1727 | 1724 | 1725 | 1725 |

Example 2-4. DSC Analysis

Figure 6A:
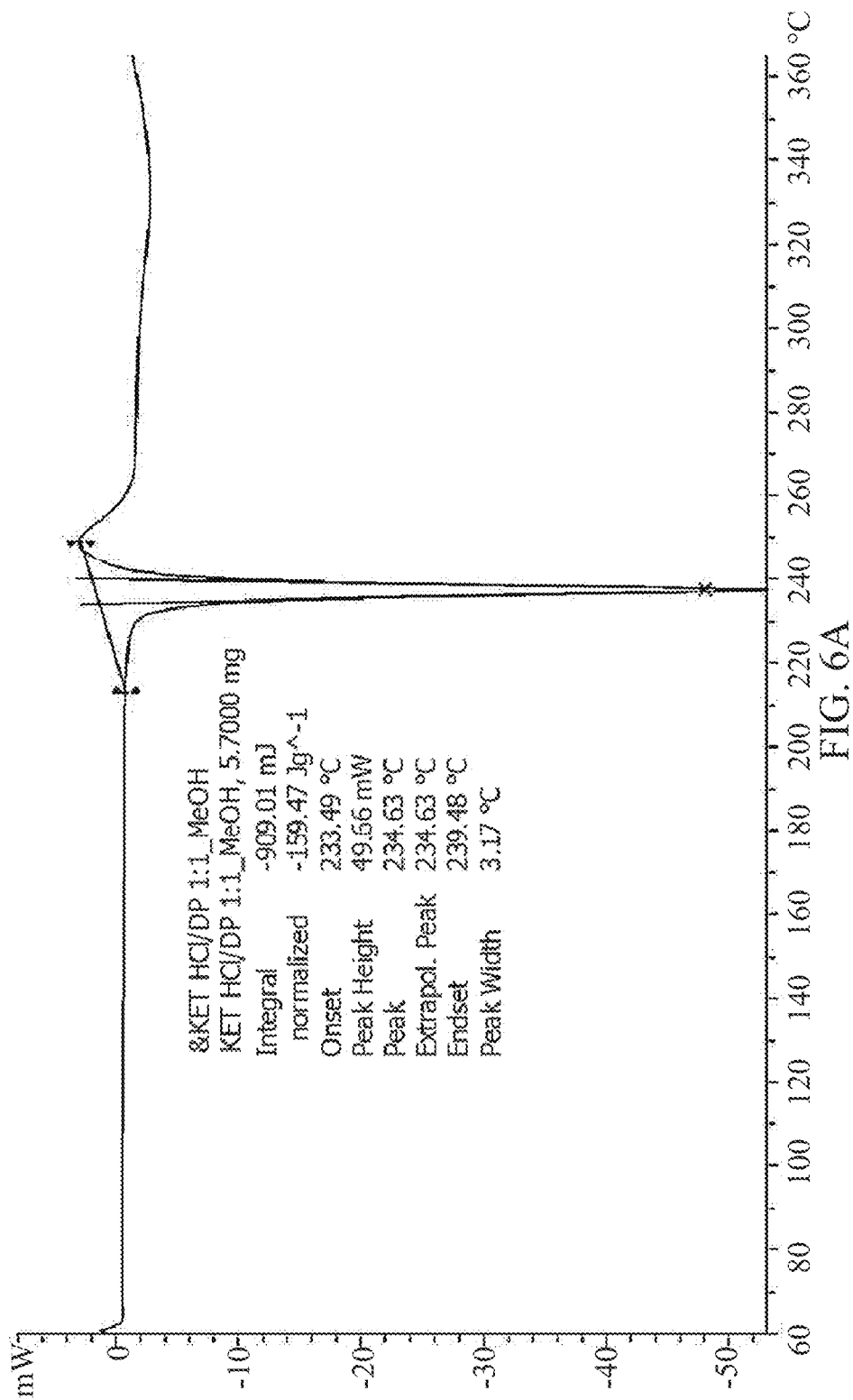
FIGS. 6A to 6F illustrate the differential scanning calorimetry patterns of R, S-ketamine pamoate, S-ketamine pamoate, and R-ketamine pamoate in crystal form (FIGS. 6A to 6C) or amorphous form (FIGS. 6D to 6F), respectively.
Figure 6B:
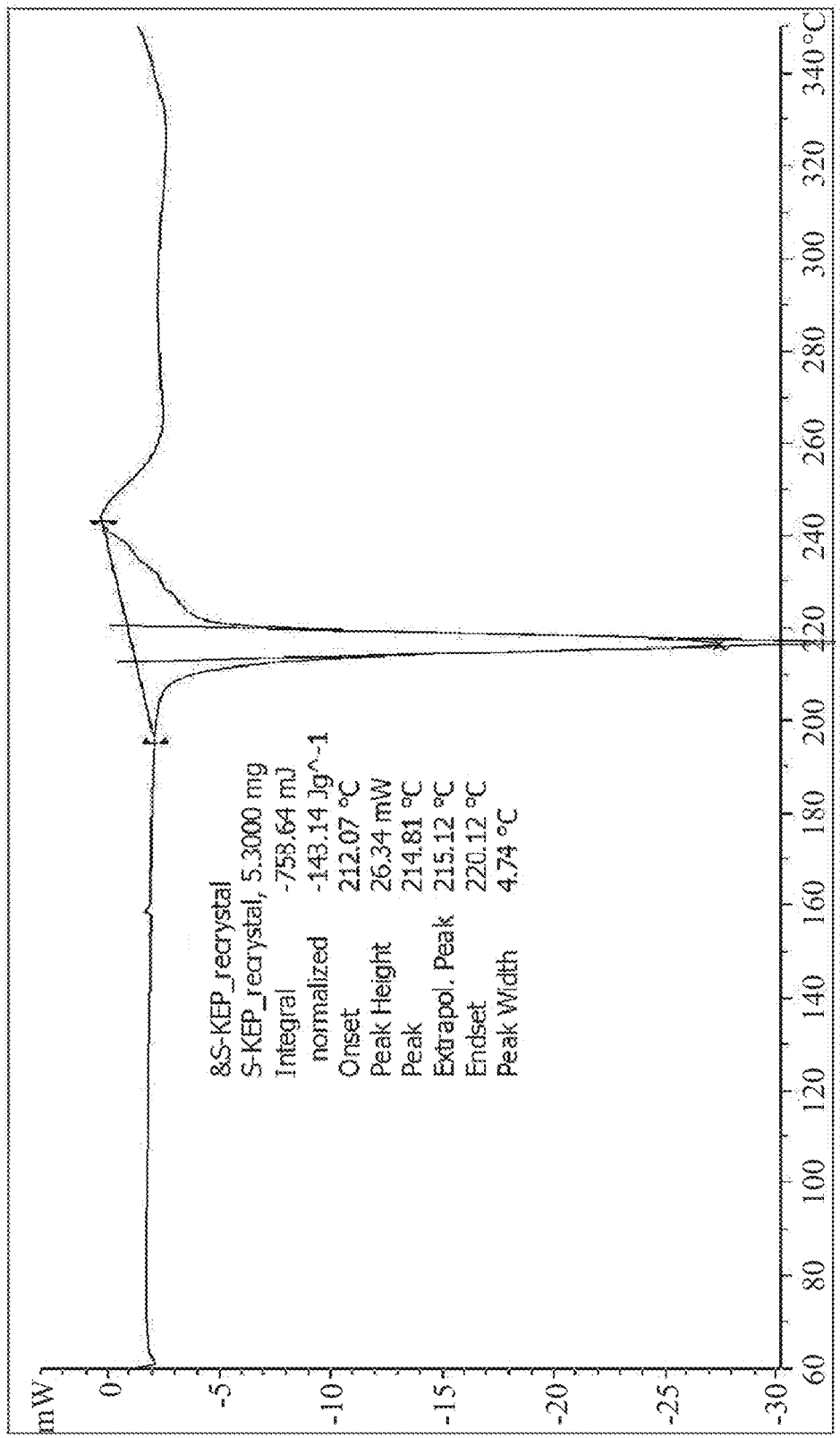
Figure 6C:
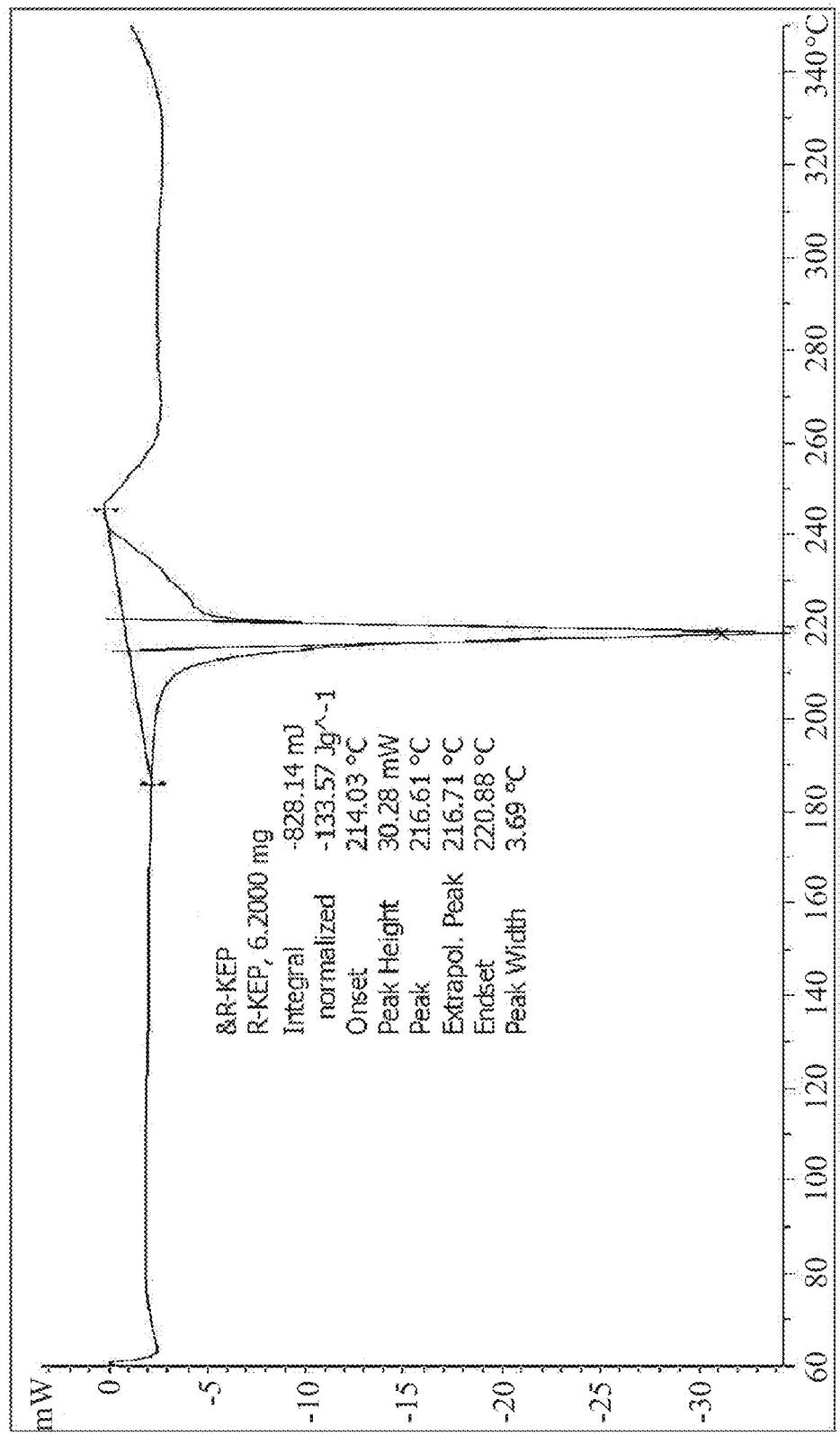
Figure 6D:
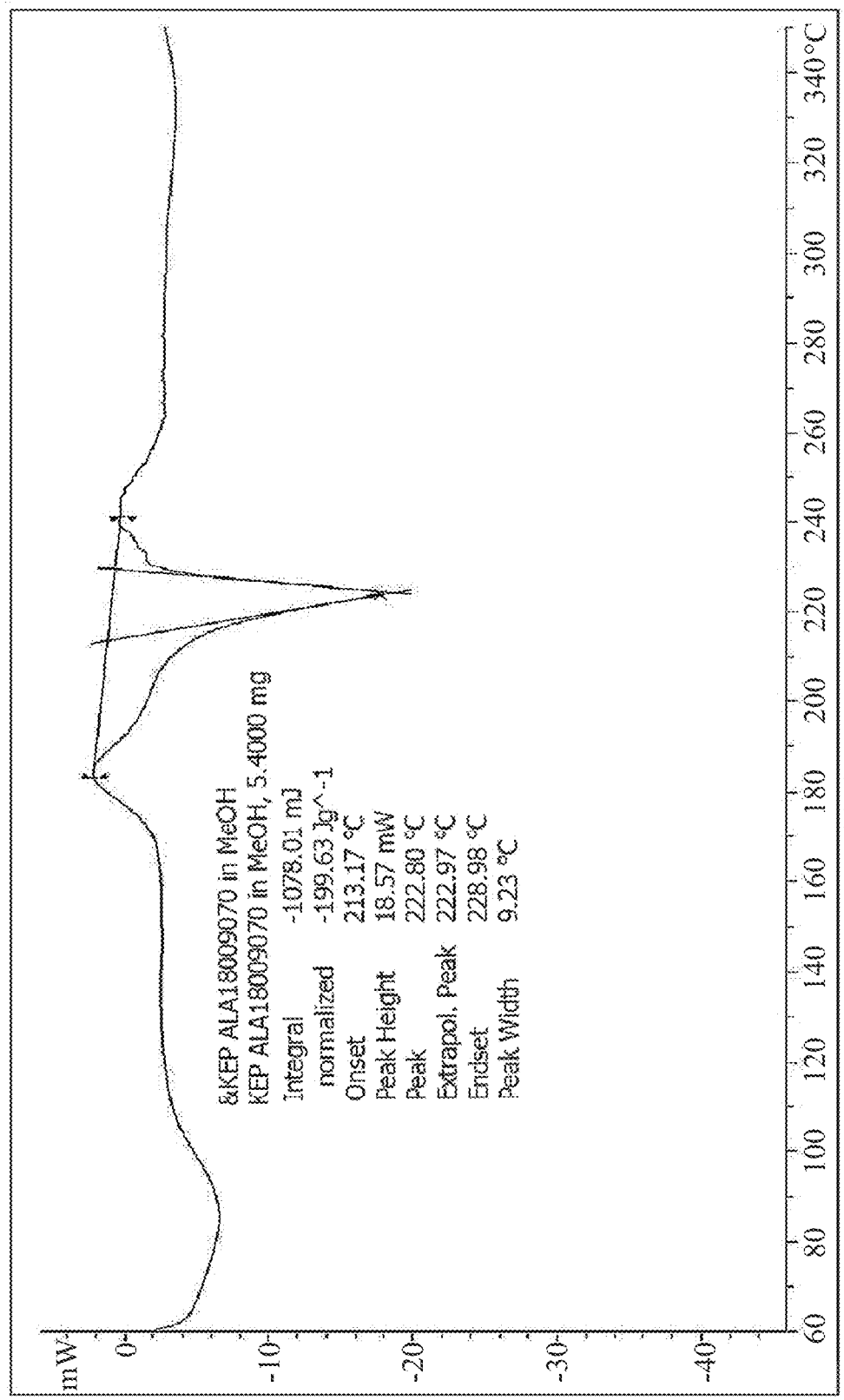
Figure 6E:
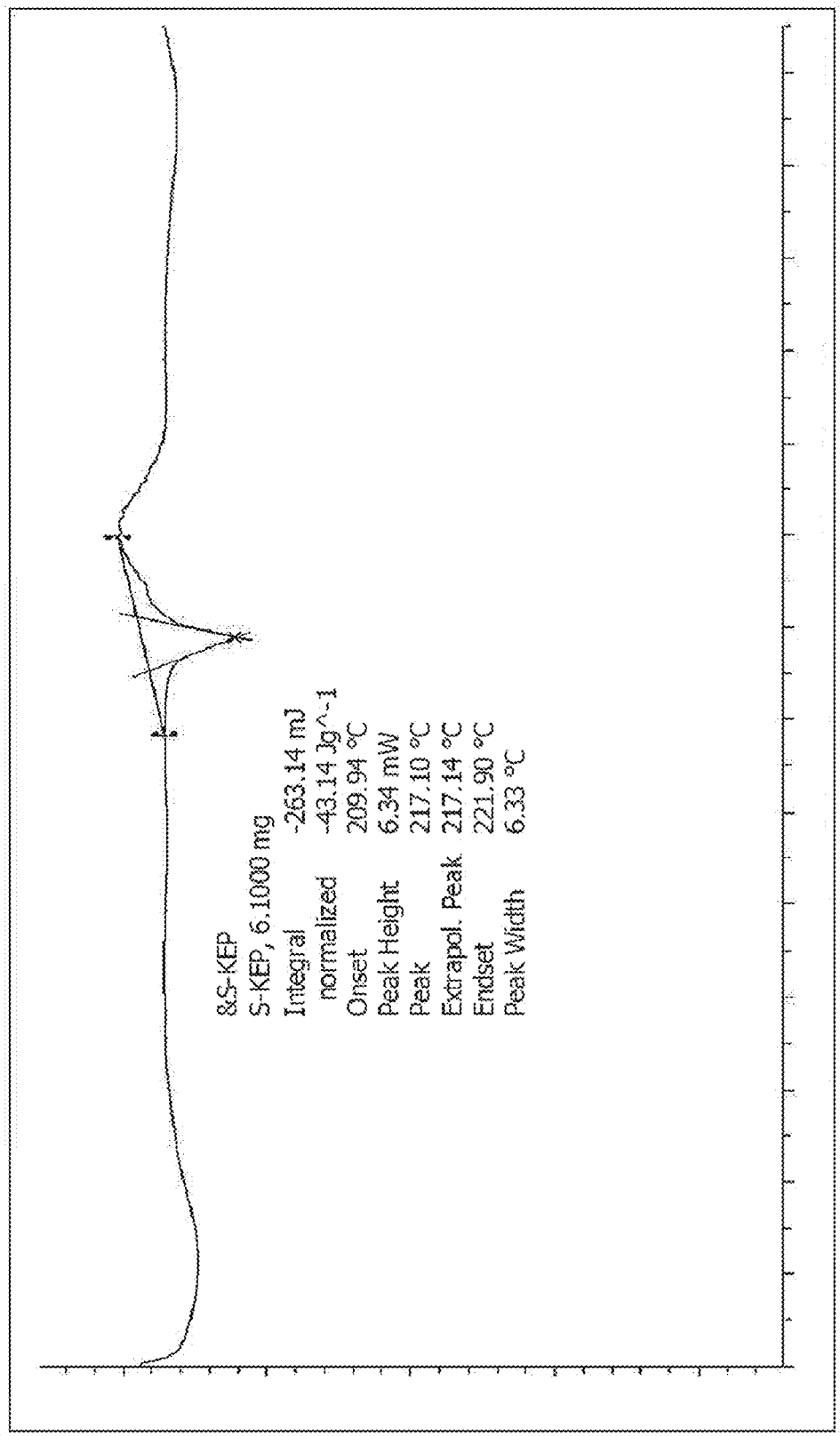
Figure 6F:
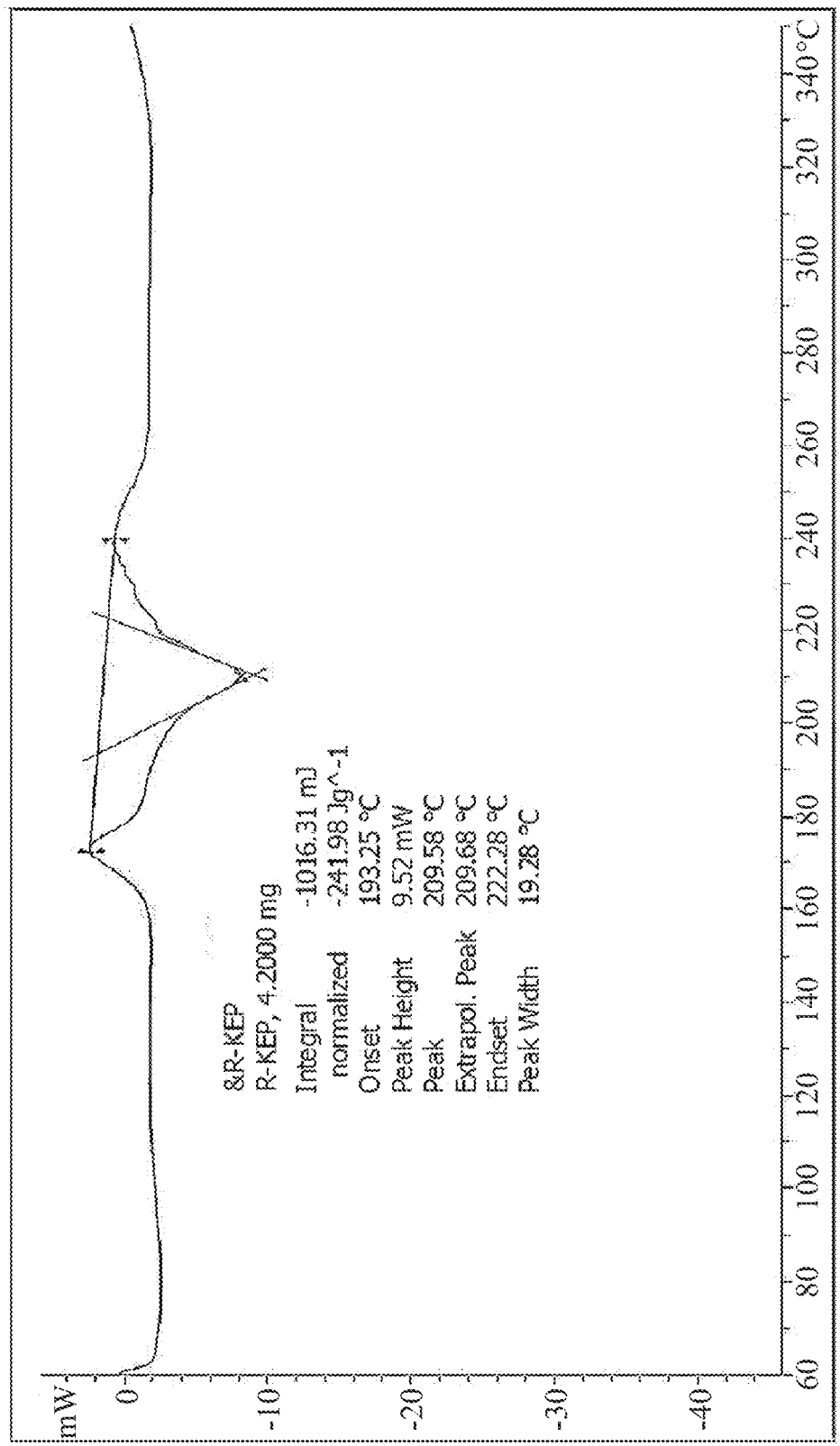

Differential scanning calorimetry (DSC) analysis of the samples of R, S-ketamine pamoate, S-ketamine pamoate, and R-ketamine pamoate exhibited a glass transition at approximately 233° C., 212° C. and 214° C., indicating that such samples were crystal form (see FIGS. 6A to 6C). DSC analysis of R, S-ketamine pamoate sample exhibited a glass transition at approximately 213° C., indicating that the sample was amorphous (see FIG. 6D). DSC analysis of the samples of S-ketamine pamoate and R-ketamine pamoate exhibited a glass transition at approximately 210° C. and 193° C., indicating that the samples were amorphous (see FIGS. 6E and 6F). DSC analysis was performed using a Mettler Toledo DSC3 under standard conditions.

The DSC analysis for crystalline forms of S-, R-enantiomers and racemic form of ketamine pamoate were summarized in Table 5 below

TABLE 5

DSC analysis peaks of S-ketamine pamoate and R-ketamine pamoate

| No. | Compound | Onset Temperature (° C.) |
|---|---|---|
| 1 | S-ketamine pamoate (Crystal) | 212.1 |
| 2 | R-ketamine pamoate (Crystal) | 214.0 |

Example 2-5. HPLC Analysis

Figure 7A:
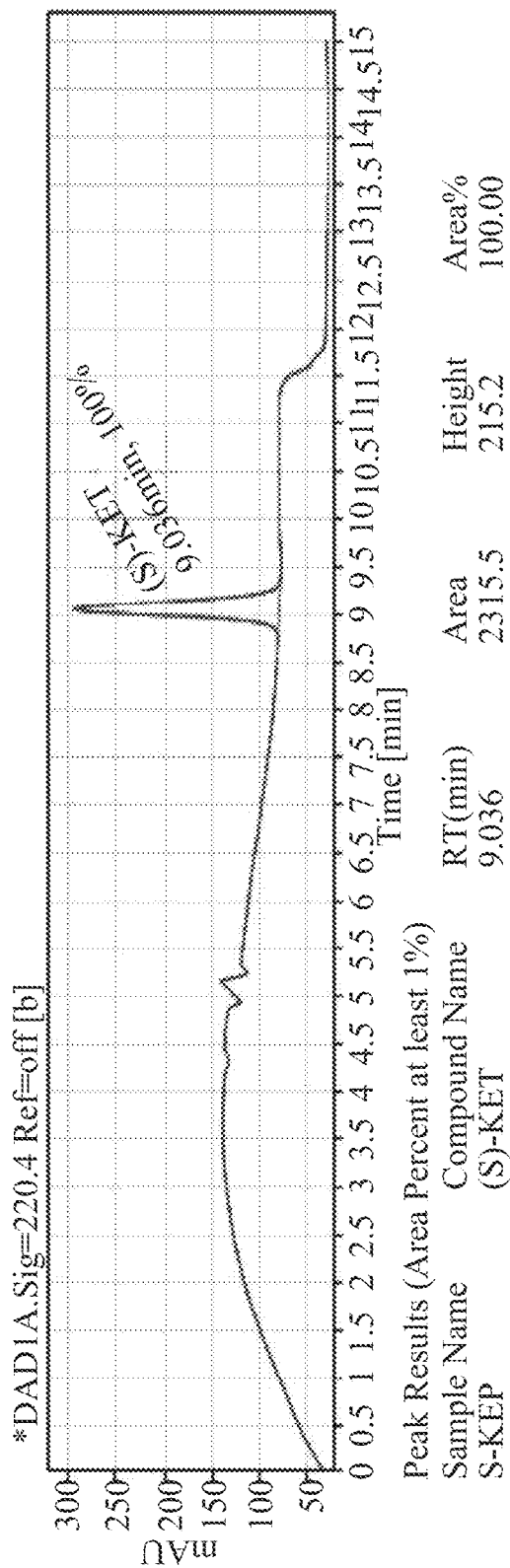
FIGS. 7A to 7C illustrate the results of high-performance liquid chromatography (HPLC) analysis of crystalline of S-ketamine pamoate and R-ketamine pamoate, and amorphous of R, S-ketamine pamoate, respectively.
Figure 7B:
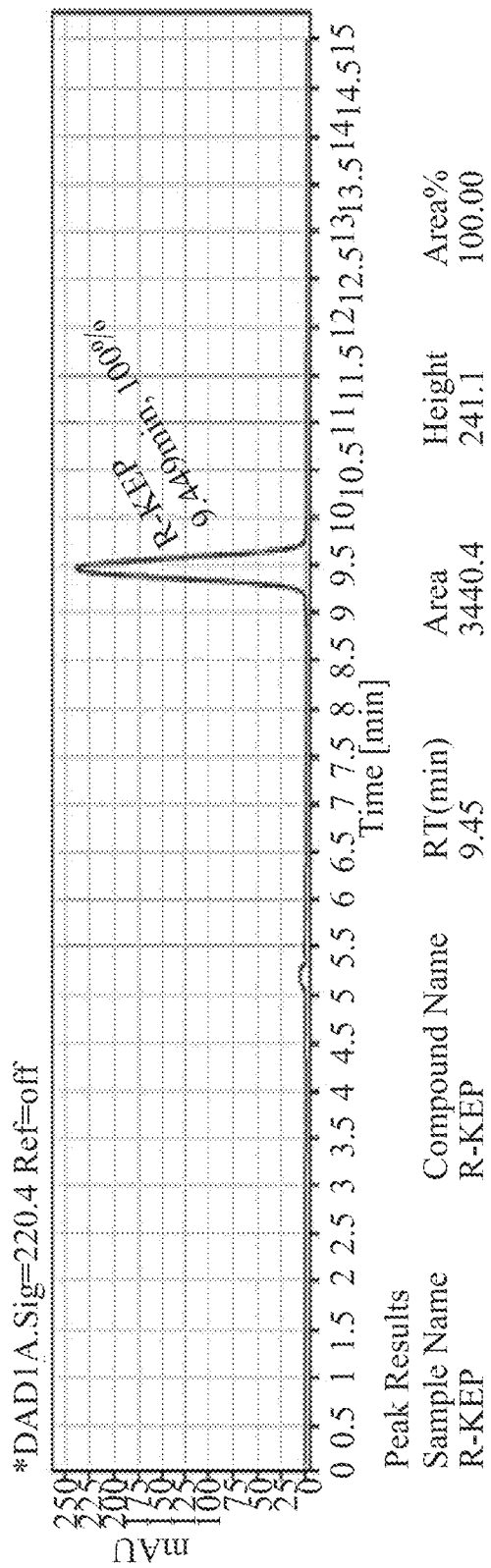
Figure 7C:
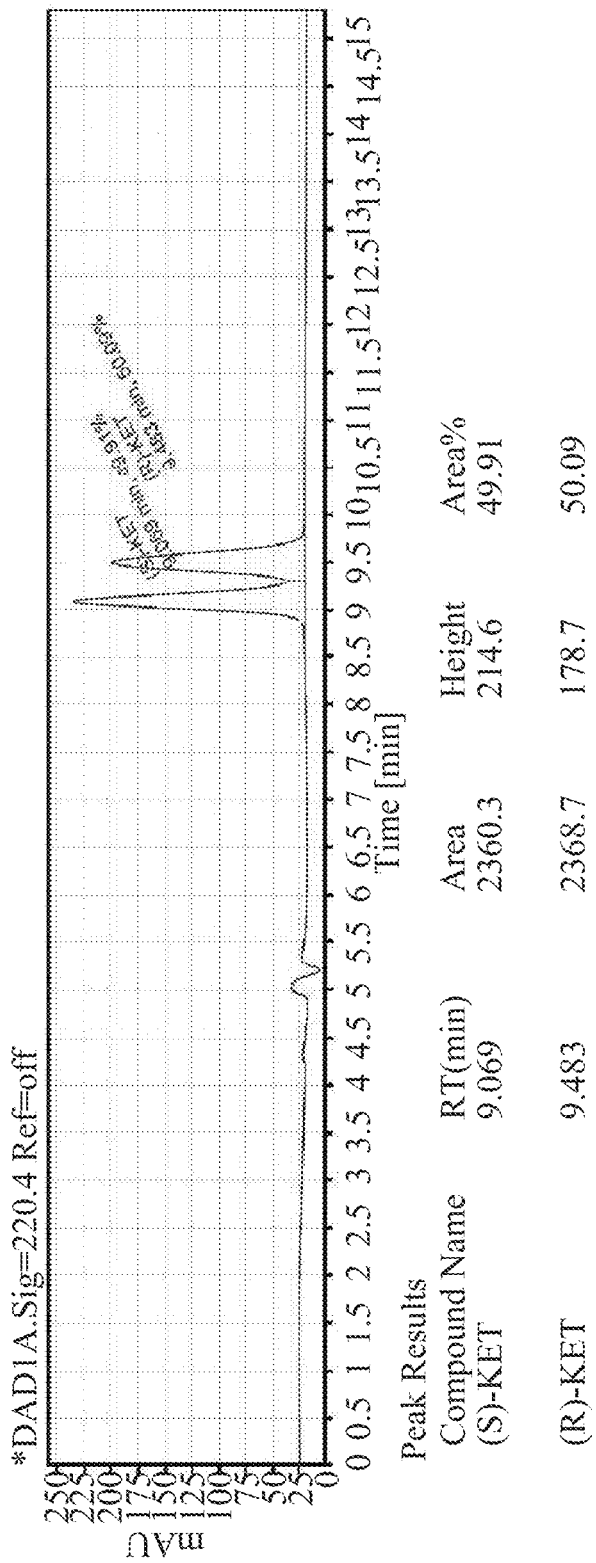

The chiral purity of S-ketamine pamoate or R-ketamine pamoate was obtained using an Agilent 1260 Infinity II high-performance liquid chromatography (HPLC) system with chiral column (Agilent Poroshell 120 Chiral-V 2.7 μm, 4.6×150 mm) under in house conditions. For HPLC analysis, S-form chiral purity was 100% (Retention Time (RT): 9.0 min) and R-form chiral purity was 100% (RT: 9.5 min). The results of HPLC analysis of S-ketamine pamoate, R-ketamine pamoate, and R, S-ketamine pamoate were shown in FIGS. 7A to 7C.

Example 2-6. Karl Fischer Analysis

Karl Fisher analysis indicated that the samples used in these examples contained no water and were not a hydrated form (water content: 0.329% for ketamine pamoate). Karl Fischer analysis was performed using Metrohm 870 KF Titrino plus under standard conditions.

Example 3. In Vivo Antidepressant Effects

Figure 8:
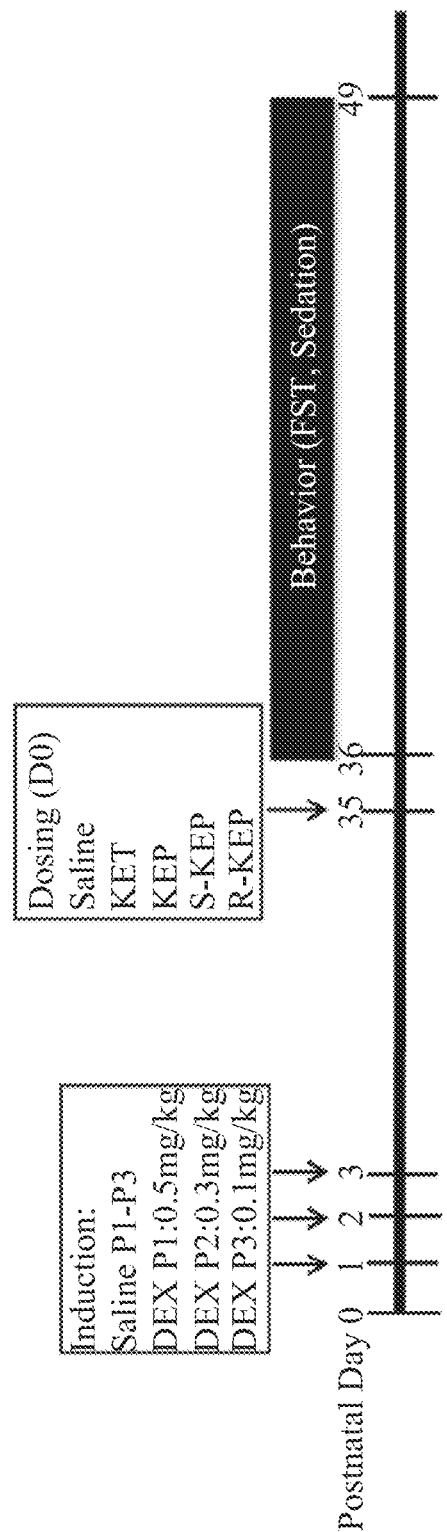
FIG. 8 is a diagram illustrating the protocol of dexamethasone (DEX)-induced depression-like animal model to evaluate the antidepressant effects of ketamine HCl (KET), R, S-ketamine pamoate (KEP), S-ketamine pamoate (S-KEP), and R-ketamine pamoate (R-KEP). ICR mice were intraperitoneally injected with saline or DEX at postnatal day 1 to 3 (P1-P3) with dose decrement of 0.5 mg/kg, 0.3 mg/kg, and 0.1 mg/kg, respectively. The drugs for each group or saline were administered subcutaneously at postnatal day 35, P35 (i.e., dosing day 0, D0), and forced swimming test (FST) was conducted on dosing day 1 (D1, P36) and dosing day 10 (P45) after drug administration. Evaluation of sedation behavior was also conducted by sedation rating scale from the time immediately post injection to dosing day 14 (P49) after drug administration.

A depression-like animal model induced by dexamethasone (hereinafter abbreviated as DEX) was used to evaluate the antidepressant effects of ketamine HCl (KET), R, S-ketamine pamoate (KEP), S-ketamine pamoate (S-KEP), and R-ketamine pamoate (R-KEP) at an equivalent dose (120 mg/kg of ketamine free-base). Protocol of this study was shown in FIG. 8 and described below.

Neonatal ICR mice (BioLASCO, Taipei, Taiwan) were intraperitoneally injected with saline or DEX on postnatal day 1, 2, and 3 (P1, P2, and P3) at doses of 0.5 mg/kg, 0.3 mg/kg, and 0.1 mg/kg, respectively. The mice received saline were called as Control group, and the mice received DEX were divided into the groups of KET, KEP, S-KEP, R-KEP and Saline (n=10 to 14 mice in each group). The dugs were then subcutaneously injected into mice of the corresponding groups at postnatal day 35, while the mice of the Control and Saline groups were injected with equal volumes of 0.9% saline. Drugs for administration were prepared in phosphate-buffered saline (PBS), and then well mixed by high speed vortex before injection.

Antidepressant effects were evaluated by forced swimming test (FST), which performed on dosing day 1 (P36) and dosing day 10 (P45) after drug administration. The mice of all groups were trained for swimming before drug administration. During the FST, mice were individually placed into 5 L glass cylinders (height 27 cm, diameter 18 cm) filled with 4 L of water (23±1° C.). The total duration of immobility time during 5 minutes of FST was observed. Results were presented as mean±SEM. Student's t-test was utilized to analyze Saline group (DEX-treated mouse group injected with saline) versus the other groups at each time point. * $p<0.05$,  $p<0.01$, and * $p<0.001$ indicate significant differences compared to the Saline group.

Figure 9:
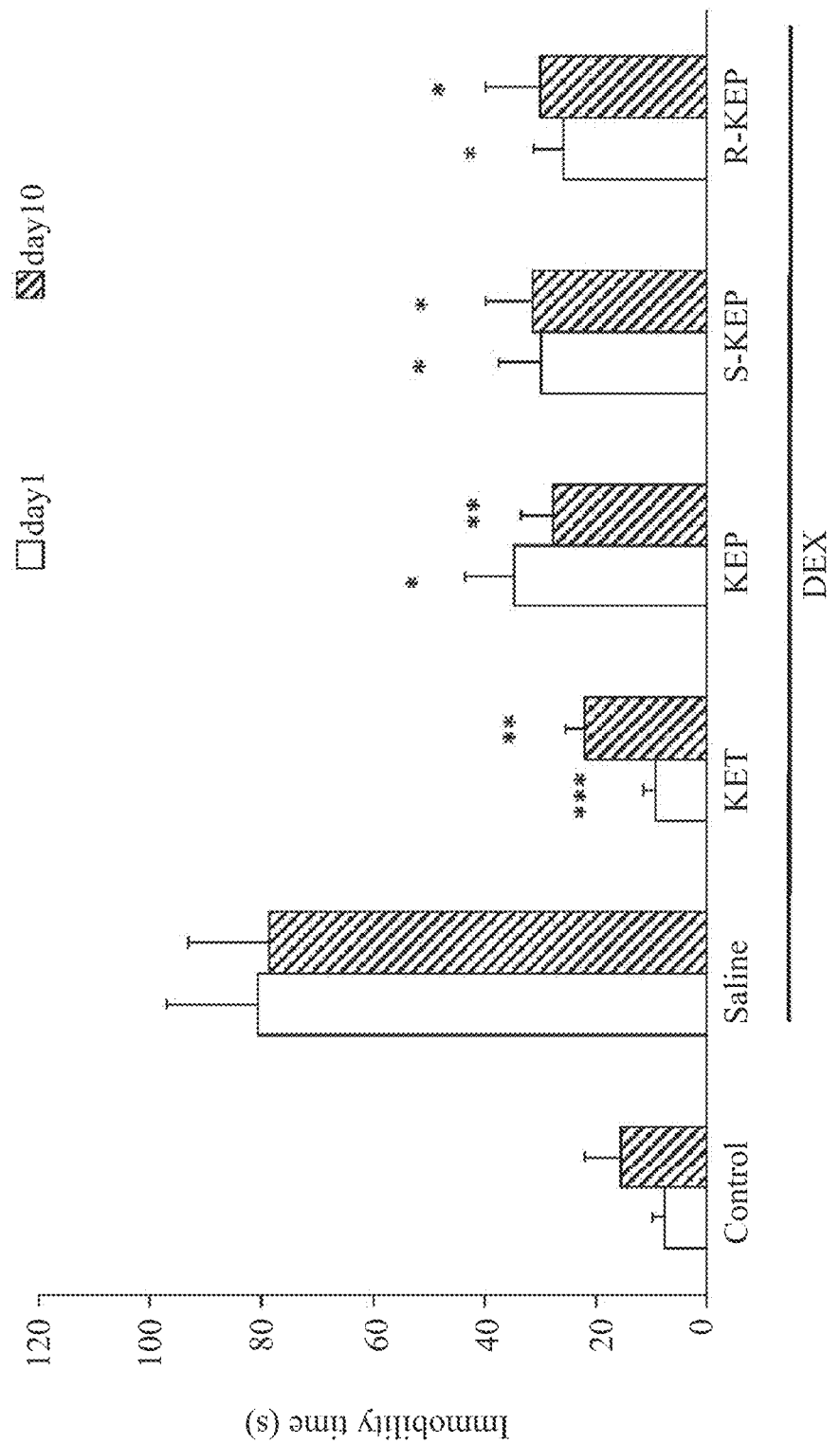
FIG. 9 is a graph showing antidepressant effects of ketamine HCl (KET), R, S-ketamine pamoate (KEP), S-ketamine pamoate (S-KEP), and R-ketamine pamoate (R-KEP) by forced swimming test (FST) on day 1 and day 10 post drug administration. * p<0.05,  p<0.01, and * p<0.001 indicate significant differences compared to the Saline group.

Mice neonatally exposed to DEX showed a significant increase of immobility time on FST compared to the Control group. The result of FST in FIG. 9 showed that all of KET, KEP, S-KEP, and R-KEP reduced the immobility times on day 1 and day 10 after administration, which were increased in DEX-treated mice.

Figure 10:
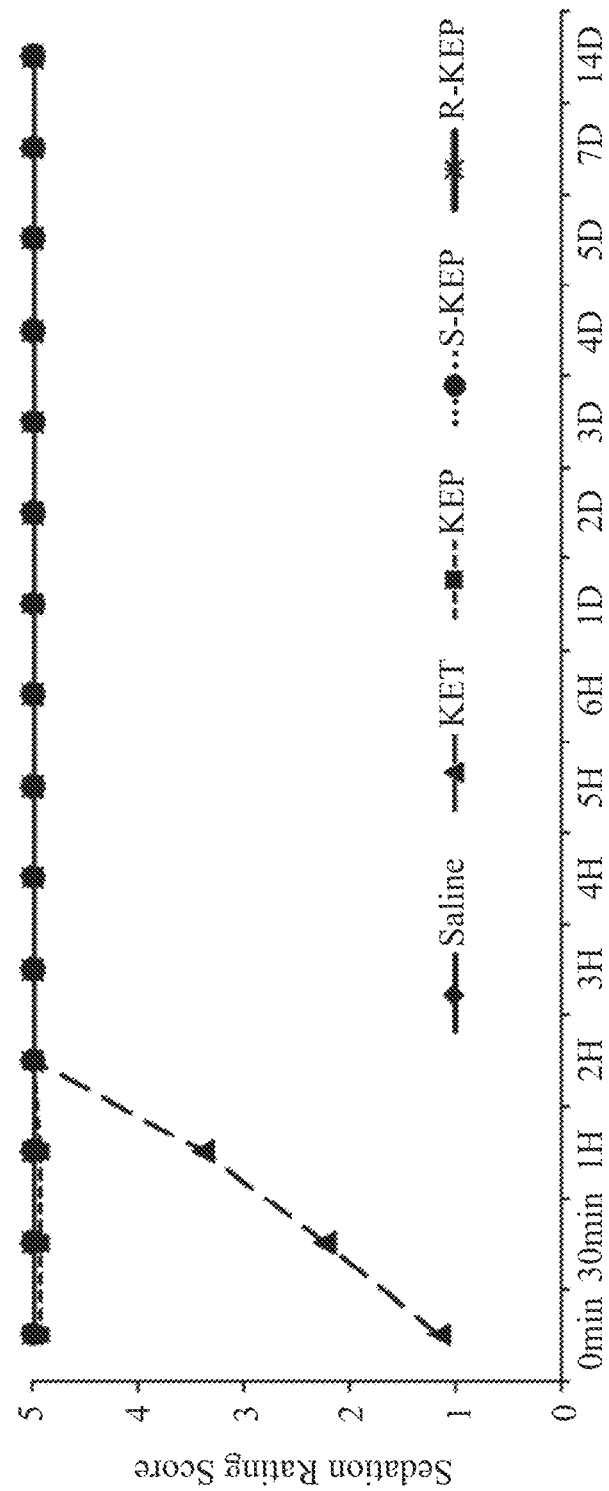
FIG. 10 is a graph showing sedation rating scores of mice treated with saline (Saline), ketamine HCl (KET), R, S-ketamine pamoate (KEP), S-ketamine pamoate (S-KEP), and R-ketamine pamoate (R-KEP) from the time immediately post injection to 14 days.

Furthermore, sedation behavior was also evaluated by rodent sedation rating scale (Table 6) immediately post drug administration to 14 days. As shown in FIG. 10, mice in the KET group immediately showed heavy sedation-related behavior after injection, and this effect was fully recovered till 2 hours post administration. Mice treated with KEP, S-KEP, and R-KEP showed normal behavior from 0 to 14 days post-injection.

TABLE 6

| Rodent sedation rating scale contents | |
|---|---|
| Score | Rating Content |
| 5-awake, active | Engaged in locomotion, rearing, head movements or grooming |
| 4-awake, inactive | Eyes fully open, head up, little to no locomotion, rearing or grooming, normal posture |
| 3-mild sedation | Eyes partly closed, head somewhat down, impaired locomotion including abnormal posture, use of only some limbs, dragging and stumbling |
| 2-moderate sedation | Head mostly or completely down, eyes partly closed, flattened posture, no spontaneous movement |
| 1-heavy sedation | Eyes mostly closed, loss of righting reflex |
| 0-asleep | Eyes fully closed, body relaxed, asleep |

In consequence, KET, KEP, S-KEP, and R-KEP all revealed rapid-onset antidepressant effects on FST after single injection at an equivalent dose (120 mg/kg of ketamine free-base), and this effect lasted for at least 10 days on DEX-treat mice. Surprisingly, in the KEP, S-KEP, and R-KEP groups, sedation or other ketamine-related psychotomimetic effects and nervous system disorders would not occur post administration, implying that KEP, S-KEP, and R-KEP had another beneficial property for being used as an antidepressant in comparison with KET.

Example 4. In Vivo Repeat-Dose Toxicology Study

Figure 11:
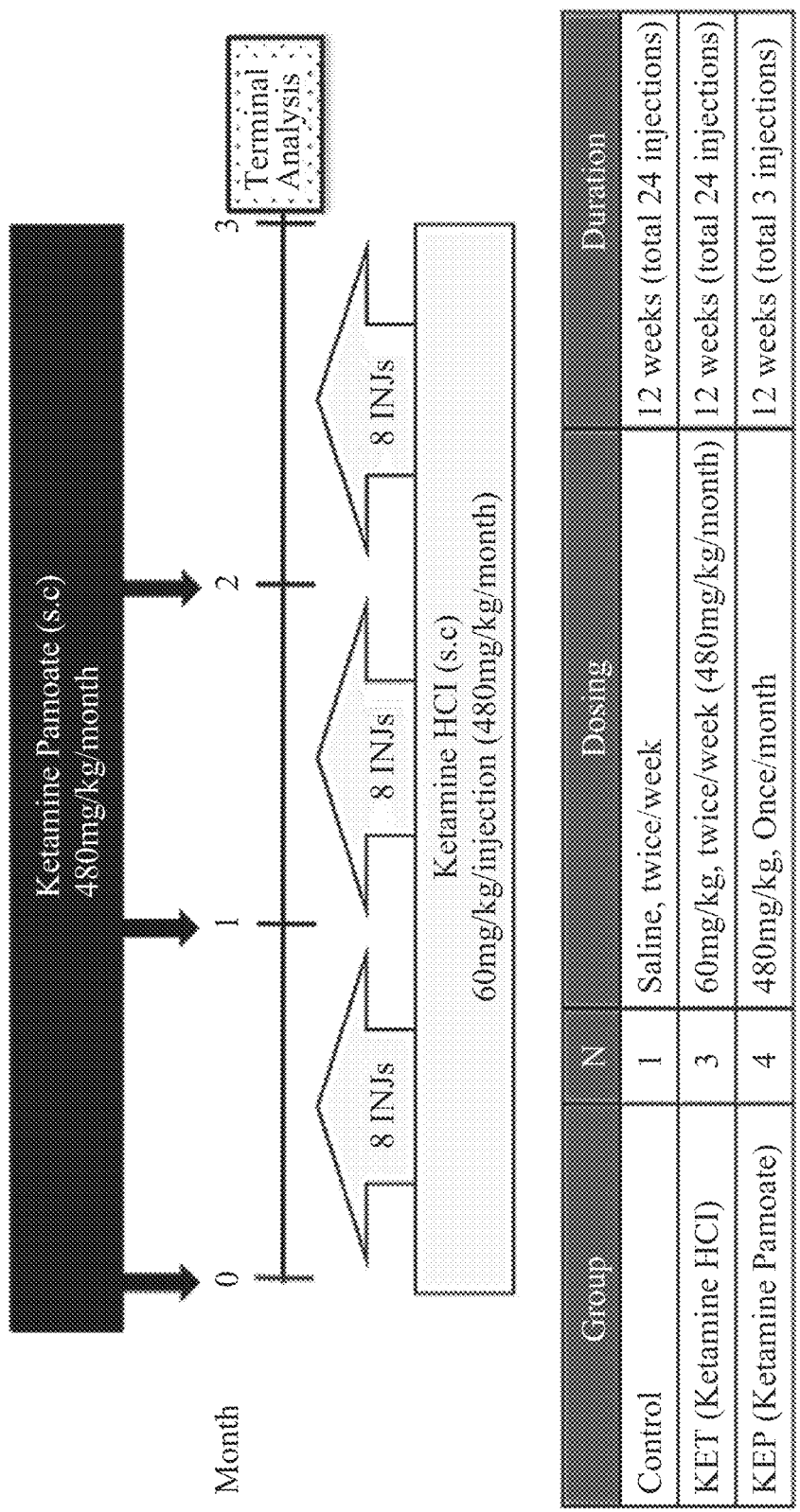
FIG. 11 is a diagram illustrating the protocol of a 3-month repeat-dose toxicology study of Control (saline), ketamine HCl (KET) and R, S-ketamine pamoate (KEP) in female Sprague Dawley (SD) rats. KET group was subcutaneously (s.c) injected twice per week of 60 mg/kg body weight, and KEP group was subcutaneously injected at dose of 480 mg/kg body weight monthly. Animals were sacrificed at Day 84 for histopathology analysis. INJs: injections.

A 3-month repeat dose toxicology study in 10-week-old female Sprague Dawley (SD) rats (BioLASCO, Taipei, Taiwan) was conducted for evaluating the toxicity reactions of ketamine HCl (KET) and R, S-ketamine pamoate (KEP) at an equivalent total dose (1440 mg/kg of ketamine free-base) for 12 weeks. Protocol of this study was shown in FIG. 11 and described below.

The rats of KET group subcutaneously received 60 mg/kg body weight twice weekly for 12 weeks. The dose of 60 mg/kg per subcutaneous injection was selected because higher dose was tested to be lethal for rats. The rats of Control group subcutaneously received an equivalent amount (as the KET group) of 0.9% saline. The rats of KEP group subcutaneously received 480 mg/kg body weight per month for 12 weeks. All animals were sacrificed for terminal toxicological analysis.

For the evaluation of the injection site, rats received ketamine HCl showed injection site erythema, which gradually became open wound after administrations, whereas rats in Control and KEP groups showed normal skin surfaces after injections.

Figure 12A:
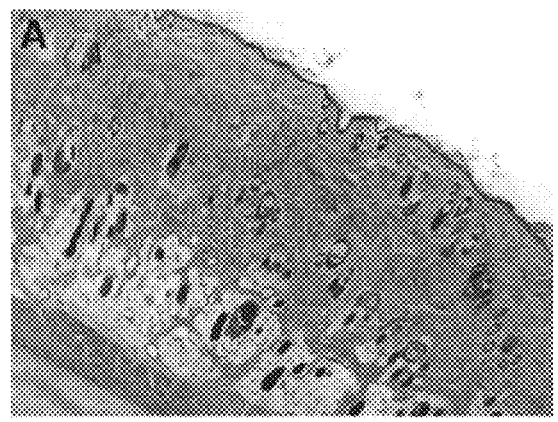
Figure 12B:
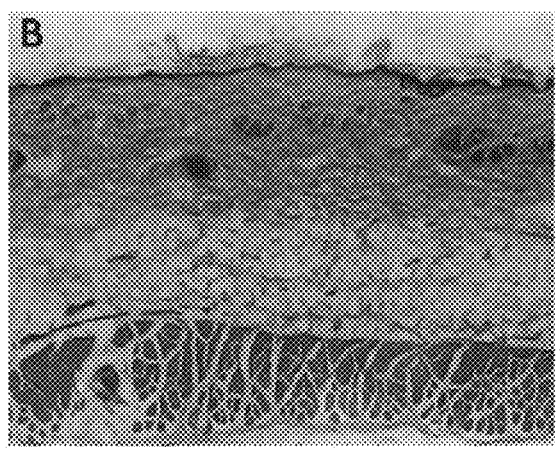
Figure 12C:
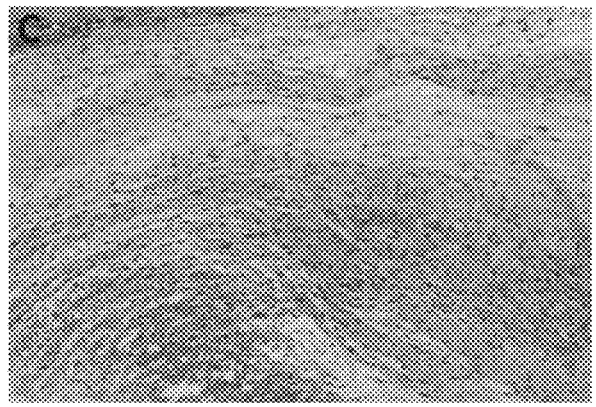
Figure 12D:
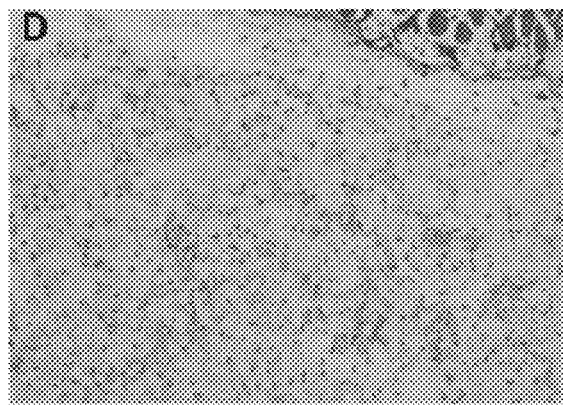
Figure 12E:
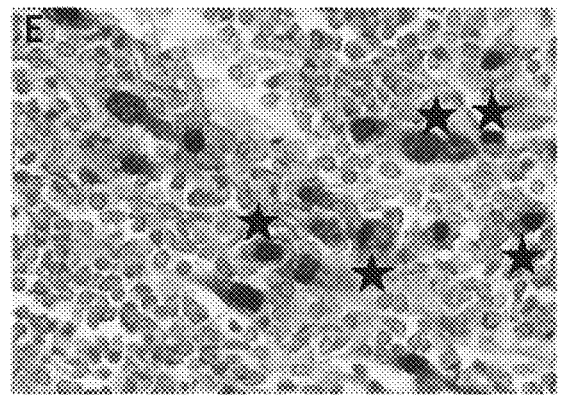
Figure 12F:
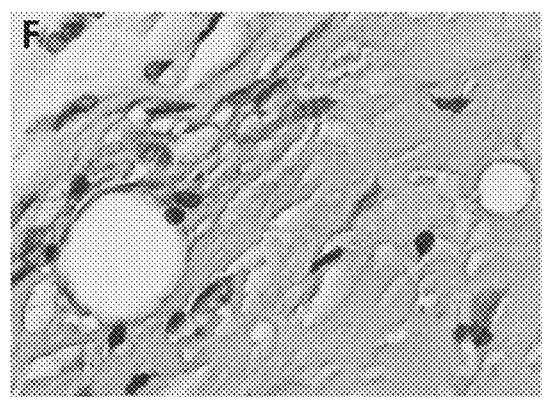

For the histopathological analysis, KET injection sites revealed morphology damage on epidermis, dermis, subcutis, and muscle tissues (FIG. 12A), and infiltration of inflammatory cells in connective tissues was found at higher magnified images (FIGS. 12C and 12E). For KEP group, histopathological analysis showed normal morphology of skin slices at injection sites (FIG. 12B). By higher magnified images, it was also found that KEP caused infiltration of inflammatory cells in connective tissues; however, the density of inflammatory cells under microscopic fields was much less than KET group (FIGS. 12D and 12F). At 400-fold magnified field (FIG. 12F), it was found that injection site of KEP group caused some focal empty cyst-like spaces, where the R, S-ketamine pamoate particles might exist and had been diffused or eliminated to the circulatory system. Ketamine pamoate particles did not induce aggregation or encapsulation of inflammatory cells.

Figure 13A:
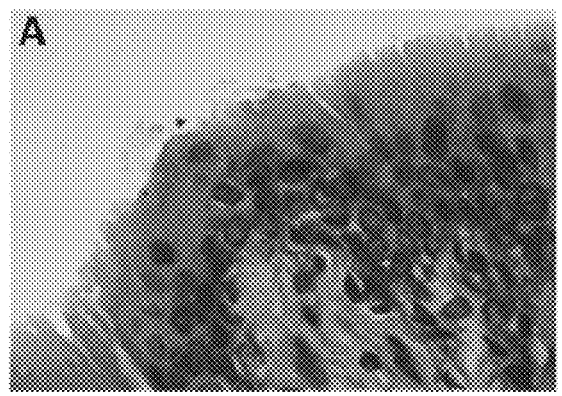
Figure 13B:
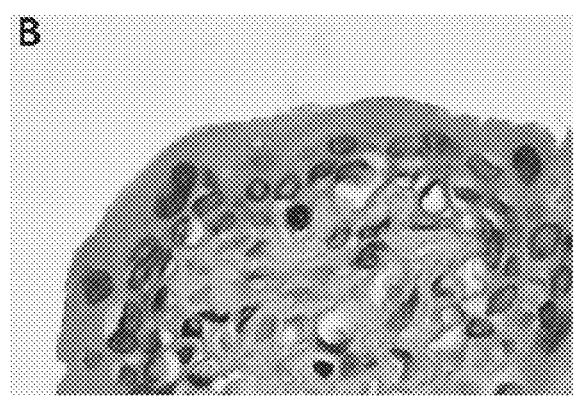
Figure 13C:
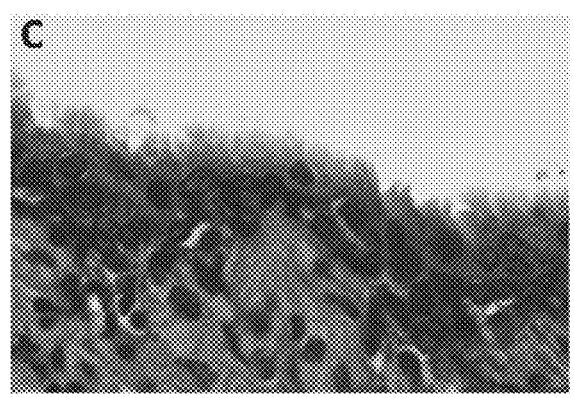
Figure 13D:
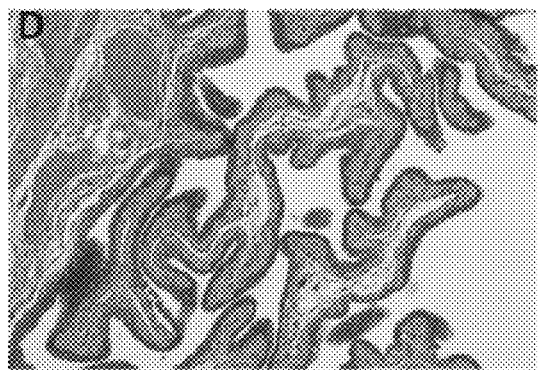
Figure 13E:
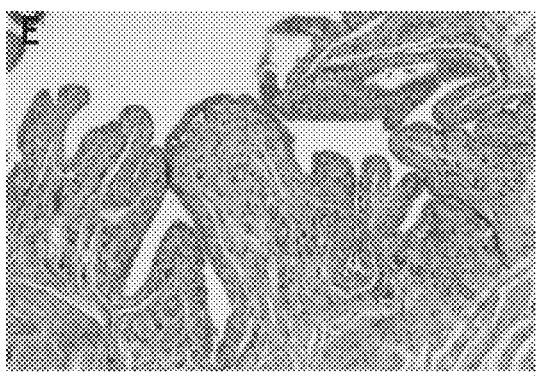
Figure 13F:
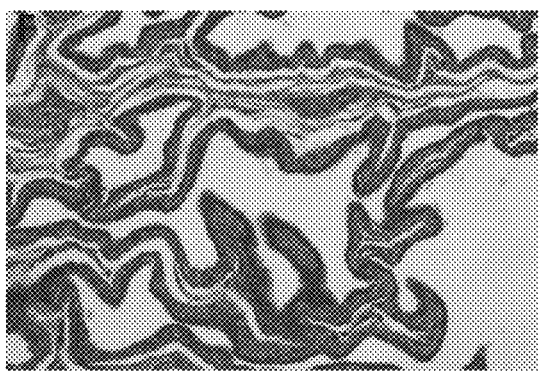

Abuse of ketamine has been reported to cause bladder cystitis [26]; therefore, histopathology analysis of bladder tissues was also conducted in this example. Bladder apical epithelial surfaces were rough in Control and KEP groups (FIGS. 13A and 13C; magnification: ×400), but smooth in KET group (FIG. 13B; magnification: ×400). In addition, Control and KEP groups had thin mucosal folds (FIGS. 13D and 13F; magnification: ×40), whereas KET group presented protrusive and enlarged mucosal folds (FIG. 13E; magnification: ×40), indicating fibrous expansion in connective tissues.

Figure 14A:
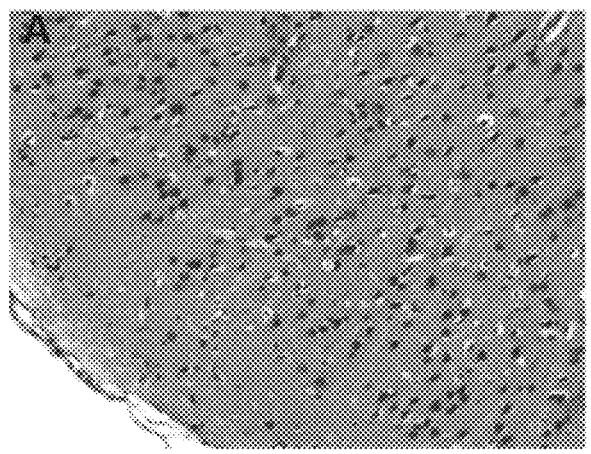
Figure 14B:
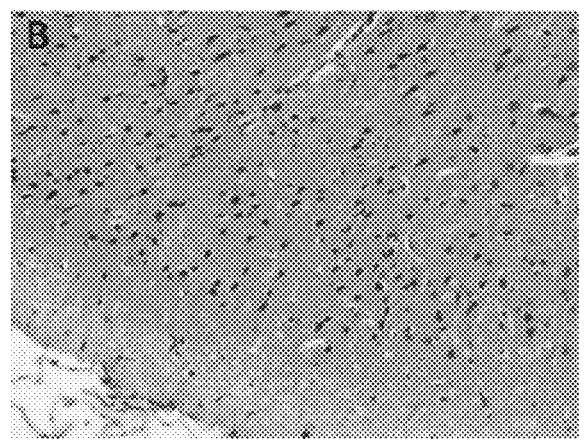
Figure 14C:
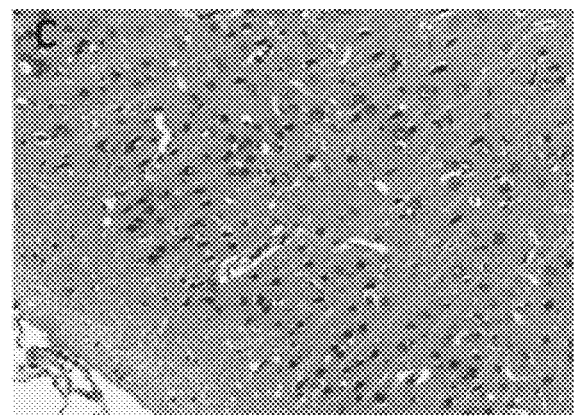
Figure 14D:
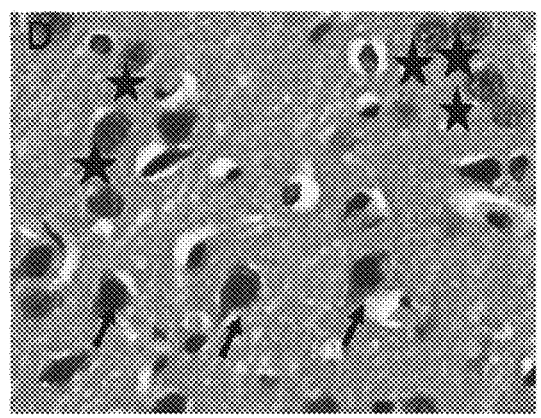
Figure 14E:
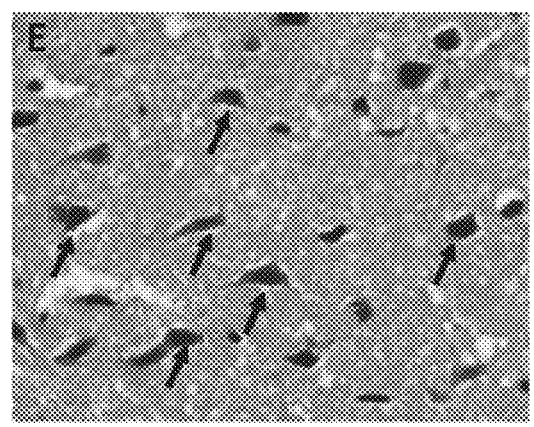
Figure 14F:
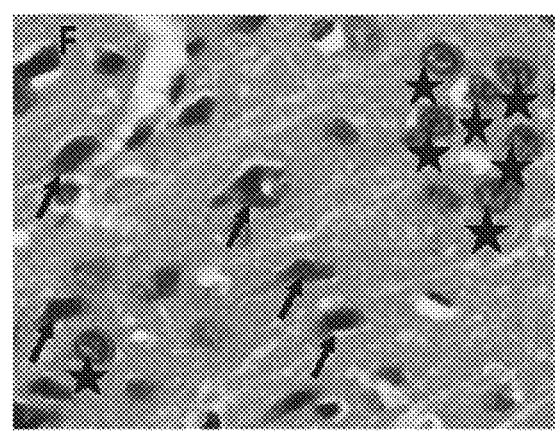

For the evaluation of the central nervous system, rat brain slices were collected for gross pathological examination. In the prefrontal cortex, granule cells were lack, and the morphology of pyramidal cells changed to be small or shrinking like in process of degradation in KET group rats (FIGS. 14B and 14E). On the other hand, the neuronal morphology in prefrontal cortex of Control and KEP rats were normal (FIGS. 14A, 14C, 14D, and 14F).

In consequence, the maximum tolerated dose (MTD) of KET via subcutaneous injection was 60 mg/kg of ketamine free-base in rats. Single subcutaneous injection of KEP at 480 mg/kg of ketamine free-base was higher than the $LD_{50}$ dose of ketamine (229 mg/kg) and was well tolerable in rats. High dose subchronic treatment of KEP for 12 weeks in rats did not cause pathological bladder and brain changes, whereas KET rats exhibited changes including bladder fibrosis and neuronal morphology alteration in brain. According to these findings, KEP specifically performed much fewer toxicity effects than KET at a total equivalent dose.

Example 5. In Vivo Injection Site Evaluation

A specific in vivo study to evaluate the injection site reaction of KEP was conducted in beagle dogs (KITAYAMA LABES, CO., LTD. Ina, Japan). Four male dogs were injected with KEP at an equivalent dose (44 mg/kg of ketamine free-base). Draize skin erythema/eschar scores (Table 7 below) were used to assess the injection site reactions at day 1, 2, 4, 8, and 15 after KEP administration.

TABLE 7

| Draize skin erythema/eschar rating scale | |
| --- | --- |
| Score | Erythema and Eschar Formation |
| 0 | No erythema |
| 1 | Very slight erythema (barely perceptible) |

TABLE 7-continued

| Draize skin erythema/eschar rating scale | |
| --- | --- |
| Score | Erythema and Eschar Formation |
| 2 | Well-defined erythema |
| 3 | Moderate to severe erythema |
| 4 | Severe erythema (beet redness) to eschar formations grading of erythema |

Previous repeat dose toxicology study in rats had proved that KEP had less injection site response both by local site observation and pathological analysis. This example showed further supporting evidence for the injection site safety of KEP in dogs. By Draize scale evaluation, all four beagle dogs had no erythema observed on injection sites from day 1 to day 15 after single high dose KEP administration (Table 8).

TABLE 8

| Individual animal injection site evaluation by Draize skin erythema/eschar rating scale | | |
| --- | --- | --- |
| Animal Number | Observation | Observation Day |
| 1001 | No erythema (score 0) | Day 1, 2, 4, 8, 15 |
| 1002 | No erythema (score 0) | Day 1, 2, 4, 8, 15 |
| 1003 | No erythema (score 0) | Day 1, 2, 4, 8, 15 |
| 1004 | No erythema (score 0) | Day 1, 2, 4, 8, 15 |

From the above, the salts of ketamine, including R, S-ketamine pamoate, S-ketamine pamoate, and R-ketamine pamoate, and the polymorphs thereof provided in the present disclosure have rapid onset and similar antidepressant effects as ketamine hydrochloride.

Surprisingly, the antidepressant effect does not accompany with sedation behavior in mice treated with R, S-ketamine pamoate, S-ketamine pamoate, and R-ketamine pamoate, whereas sedation behavior occurs in mice received ketamine HCl immediately and lasts for 2 hours post administration. Subchronic toxicity of administering R, S-ketamine pamoate for 12 weeks in rats does not cause pathological bladder and brain change, whereas rats received ketamine hydrochloride exhibit changes including bladder fibrosis and neuronal morphology alteration in brain. In addition, R, S-ketamine pamoate has milder subcutaneous injection site reaction compared to ketamine hydrochloride.

These results indicate that the salts of ketamine and the polymorphs thereof provided in the present disclosure have fewer side effects and a higher tolerable dose, that is, have higher safety than ketamine HCl and thus are useful for pharmaceutical applications.

While some of the embodiments of the present disclosure have been described in detail above, it is, however, possible for those of ordinary skill in the art to make various modifications and changes to the particular embodiments shown without substantially departing from the teaching and advantages of the present disclosure. Such modifications and changes are encompassed in the scope of the present disclosure as set forth in the appended claims.

REFERENCES

[1] Wang, R., Zhang, Z., Kumar, M., Xu, G., & Zhang, M. (2019) Neuroprotective potential of ketamine prevents developing brain structure impairment and alteration of neurocognitive function induced via isoflurane through the PI3K/AKT/GSK-3β pathway. Drug Design, Development and Therapy, 13: 501-512.

[2] Ferro, M. M., Angelucci, M. E. M., Anselmo-Franci, J. A., Canteras, N. S., & Da Cunha, C. (2007) Neuroprotective effect of ketamine/xylazine on two rat models of Parkinson's disease. Brazilian Journal of Medical and Biological Research, 40(1): 89-96.

[3] Sakai, T., Ichiyama, T., Whitten, C. W., Giesecke A. H., & Lipton J. M. (2000) Ketamine suppresses endotoxin-induced NF-kB expression. Can. J. Anesth., 47: 1019-1024.

[4] Zanos, P., Moaddel, R., Morris, P. J., Riggs, L. M., Highland, J. N., Georgiou, P., Pereira E. F. R., Albuquerque E. X., & Thomas C. J., Zarate C. A. Jr., Gould T. D. (2018) Ketamine and Ketamine Metabolite Pharmacology: Insights into Therapeutic Mechanisms. Pharmacological Reviews, 70(3): 62-660.

[5] Kenji Hashimoto (2019) Application of R-ketamine and salt thereof as pharmaceuticals. U.S. Pat. No. 10,406,121 B2.

[6] Guitton M., Puel J. L., & Pujol R. (2012) Methods for the treatment of tinnitus induced by cochlear excitotoxicity. U.S. Pat. No. 8,268,866 B2.

[7] Diazgranados N., Ibrahim L., Brutsche N. E., Newberg A., Kronstein P., Khalife S., Kammerer W. A., Quezado Z., Luckenbaugh D. A., Salvadore G., Machado-Vieira R., Manji H. K., & Zarate C. A. Jr. (2010) A randomized add-on trial of an N-methyl-D-aspartate antagonist in treatment-resistant bipolar depression. Arch. Gen. Psychiatry, 67: 793-802.

[8] Bloch M. H., Wasylink S., Landeros-Weisenberger A., Panza K. E., Billingslea E., Leckman J. F., Krystal J. H., Bhagwagar Z., Sanacora G., & Pittenger C. (2012) Effects of ketamine in treatment-refractory obsessive-compulsive disorder. Biol. Psychiatry, 72(II): 964-970.

10 [9] Rodriguez C. I., Kegeles L. S., Levinson A., Feng T., Marcus S. M., Vermes D., Flood P., & Simpson H. B. (2013) Randomized controlled crossover trial of ketamine in obsessive-compulsive disorder: proof-of-concept. Neuropsychopharmacology, 38: 2475-83.

[10] Feder A., Parides M. K., Murrough J. W., Perez A. M., Morgan J. E., Saxena S., Kirkwood K., Aan Het Rot M., Lapidus K. A., Wan L. B., Losifescu D., & Charney D. S. (2014) Efficacy of intravenous ketamine for treatment of chronic posttraumatic stress disorder: a randomized clinical trial. JAMA Psychiatry, 71: 681-688.

[11] DiazGranados N., Ibrahim L. A., Brutsche N. E., Ameli R., Henter I. D., Luckenbaugh D. A., Machado-Vieira R., Zarate C. A. Jr. (2010) Rapid resolution of suicidal ideation after a single infusion of an N-methyl-D-aspartate antagonist in patients with treatment-resistant major depressive disorder. J. Clin. Psychiatry 71(12): 1605-1611.

[12] Wink L. K., O'Melia A. M., Shaffer R. C., Pedapati E., Friedmann K., Schaefer T., & Erickson C. A. (2014) Intranasal ketamine treatment in an adult with autism spectrum disorder. J. Clin. Psychiatry, 75(8): 835-836.

[13] Krystal J. H., Sanacora G., & Duman R. S. (2013) Rapid-acting glutamatergic antidepressants: the path to ketamine and beyond. Biol. Psychiatry, 73: 1133-1141.

[14] Domino E. F. (2010) Taming the ketamine tiger. 1965. Anesthesiology, 113: 678-686.

[15] Lauritsen, C., Mazuera, S., Lipton, R. B., & Ashina, S. (2016) Intravenous ketamine for subacute treatment of refractory chronic migraine: a case series. The Journal of Headache and Pain, 17(1): 106.

[16] Goyal, S. & Agrawal, A. (2013) Ketamine in status asthmaticus: A review. Indian journal of critical care medicine: peer-reviewed, official publication of Indian Society of Critical Care Medicine, 17(3): 154-161.

[17] Taylor, J. H., Landeros-Weisenberger, A., Coughlin, C., Mulqueen, J., Johnson, J. A., Gabriel, D., Reed M. O., Jakubovski E. & Bloch, M. H. (2018) Ketamine for social anxiety disorder: a randomized, placebo-controlled crossover trial. Neuropsychopharmacology, 43(2): 325-333.

[18] Jones, J. L., Mateus, C. F., Malcolm, R. J., Brady, K. T., & Back, S. E. (2018) Efficacy of ketamine in the treatment of substance use disorders: a systematic review. Frontiers in Psychiatry, 9: 277.

[19] Synowiec A. S., Singh D. S., Yenugadhati V., Valeriano J. P., Schramke C. J., & Kelly K. M. (2013) Ketamine use in the treatment of refractory status epilepticus. Epilepsy Research. 105(1-2): 183-188.

[20] Proescholdt M., Heimann A. & Kempski O. (2001). Neuroprotection of S(+) ketamine isomer in global forebrain ischemia. Brain Research, 904(2): 245-251.

[21] Mills, I., Park, G. & Manara, A. & Merriman, R (1998). Treatment of compulsive behaviour in eating disorders with intermittent ketamine infusions. QJM: Monthly Journal of the Association of Physicians, 91: 493-503.

[22] Lascelles K., Marzano L., Brand F., Trueman H., McShane R. M. D., & Hawton K. (2019) Effects of ketamine treatment on suicidal ideation: a qualitative study of patients' accounts following treatment for depression in a UK ketamine clinic. BMJ Open, 9: e029108.

[23] Canuso C. M., Singh J. B., Fedgchin M., Alphs L., Lane R, Lim P., Pinter C., Hough D., Sanacora G., Manji H. & Drevets W. C. (2018) Efficacy and safety of intranasal esketamine for the rapid reduction of symptoms of depression and suicidality in patients at imminent risk for suicide: results of a double-blind, randomized, placebo-controlled study. American Journal of Psychiatry, 175(7): 620-630.

[24] Jassen Research and Development, LLC. (2019). Esketamine nasal spray for patients with treatment-resistant depression. US FDA Advisory Committee Briefing Document.

[25] Li, Q., Chan, W. M., Rudd, J. A., Wang, C. M., Lam, P. Y., Wai, M. S., Wood, D. M., Dargan, P. I., & Yew, D. T. (2013). Novel psychoactive substances: classification, pharmacology and toxicology. Book 2013. Chapter 12—Ketamine.

[26] Jhang, J., Hsu, Y. & Kuo, H. (2015) Possible pathophysiology of ketamine-related cystitis and associated treatment strategies. Int. J. Urol., 22: 816-825.

What is claimed is:

1. A pamoate salt of ketamine having a stoichiometry of 2:1 of ketamine to pamoate.

2. The pamoate salt of ketamine according to claim 1, which is:

a pamoate salt of R, S-ketamine represented by Formula (I) below:

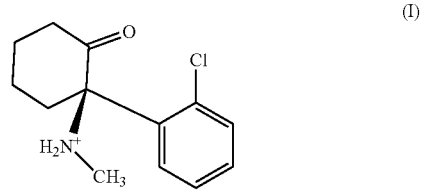

a pamoate salt of S-ketamine represented by Formula (II) below:

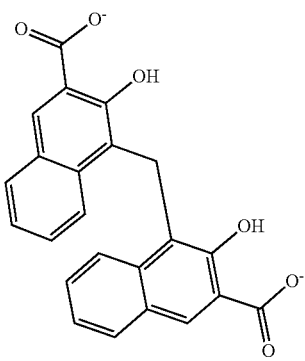
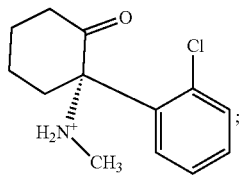

(II)

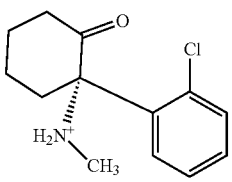

or a pamoate salt of R-ketamine represented by Formula (III) below:

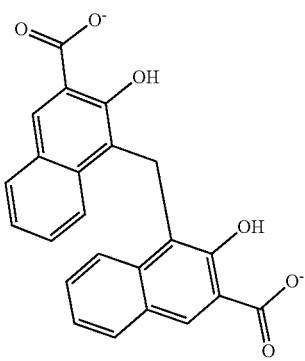
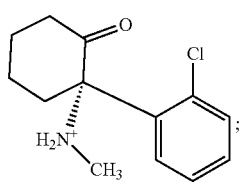

(III)

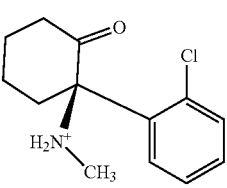

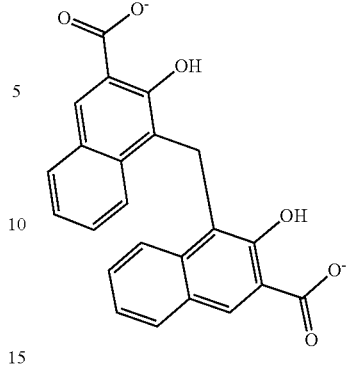
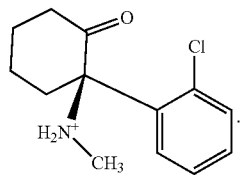

3. The pamoate salt of ketamine according to claim 1, which is amorphous.

4. The pamoate salt of ketamine according to claim 1, which is crystalline having an X-ray powder diffraction (XRPD) pattern comprising one or more 2θ values ±0.2 2θ selected from 6.0, 10.7, 11.6, 12.0, 13.0, 14.7, 15.0, 19.6, 22.2, 25.2 and 30.3.

5. The pamoate salt of ketamine according to claim 2, wherein the pamoate salt of R, S-ketamine is crystalline having an XRPD pattern represented by at least one of the following:
   (i) the XRPD pattern comprising one or more 2θ values ±0.2 2θ selected from 6.0, 8.6, 10.7, 11.6, 12.0, 13.0, 14.7, 15.0, 15.3, 17.9, 18.6, 19.6, 20.0, 21.1, 21.6, 22.2, 23.3, 24.4, 25.2, 25.9, 26.9, 28.6, 29.7, 30.3, 32.4, 34.0 and 36.6; and
   (ii) the XRPD pattern shown in FIG. 2A.

6. The pamoate salt of ketamine according to claim 2, wherein the pamoate salt of S-ketamine is crystalline having an XRPD pattern represented by at least one of the following:
   (i) the XRPD pattern comprising one or more 2θ values ±0.2 2θ selected from 6.0, 10.8, 11.7, 12.0, 12.6, 13.1, 14.6, 15.1, 18.2, 19.2, 19.7, 20.1, 22.0, 22.8, 23.3, 23.7, 24.1, 24.7, 25.2, 27.3, 30.1, 31.6, 45.4, 56.4 and 75.2; and
   (ii) the XRPD pattern shown in FIG. 2B.

7. The pamoate salt of ketamine according to claim 2, wherein the pamoate salt of R-ketamine is crystalline having an XRPD pattern represented by at least one of the following:
   (i) the XRPD pattern comprising one or more 2θ values ±0.2 2θ selected from 6.0, 10.8, 11.7, 12.0, 12.6, 13.1, 14.6, 15.0, 18.2, 19.3, 19.7, 20.6, 22.0, 22.9, 23.6, 24.1, 24.7, 25.2, 25.9, 27.3, 30.1, 31.6, 45.4, 56.4 and 75.2; and
   (ii) the XRPD pattern shown in FIG. 2C.

8. The pamoate salt of ketamine according to claim 1, which has a purity of greater than 95%.

9. A method for treating a central nervous system (CNS) disease, comprising administering to a subject in need thereof an effective amount of a pharmaceutical composition comprising the pamoate salt of ketamine according to claim 1 and a pharmaceutically acceptable excipient thereof.

10. The method according to claim 9, wherein the CNS disease is selected from the group consisting of major depressive disorder (MDD), MDD with imminent risk of suicidal ideation, treatment-resistant depression (TRD), bipolar disorder, obsessive-compulsive disorder, posttraumatic stress disorder (PTSD), autism spectrum disorder, tinnitus, refractory chronic migraine, asthma, anxiety, substance use disorders, alcohol use disorder, eating disorders, refractory status epilepticus, brain ischemia, Alzheimer's disease, Parkinson's disease, stroke, traumatic brain injury, multiple sclerosis, and pain.

11. The method according to claim 9, wherein the treatment of the CNS disease onsets within 24 hours and lasts for at least 10 days after administration of the pharmaceutical composition.

12. A method for anesthetizing a subject in need thereof, comprising administering to the subject an effective amount of a pharmaceutical composition comprising the pamoate salt of ketamine according to claim 1 and a pharmaceutically acceptable excipient thereof.

13. The method according to claim 12, wherein the anesthesia onsets within 24 hours and lasts for at least 10 days after administration of the pharmaceutical composition.

\* \* \* \* \*